United States Patent
Shaw et al.

(10) Patent No.: US 9,272,019 B2
(45) Date of Patent: Mar. 1, 2016

(54) MIC-1 FUSION PROTEINS AND USES THEREOF

(71) Applicant: Novo Nordisk A/S, Bagsvaerd (DK)

(72) Inventors: Allan Christian Shaw, Copenhagen N (DK); Charlotte Helgstrand, Bagsvared (DK); Michael Paolo Bastner Sandrini, Bagsvaerd (DK); Sebastian Beck Joergensen, Bagsvaerd (DK); Henning Thoegersen, Farum (DK); Kristian Sass-Oerum, Koebenhavn (DK); Sven Hastrup, Koebenhavn (DK); Kim Vilbour Andersen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/742,159

(22) Filed: Jun. 17, 2015

(65) Prior Publication Data

US 2016/0015784 A1   Jan. 21, 2016

(30) Foreign Application Priority Data

Jun. 24, 2014   (EP) ..................................... 14173664

(51) Int. Cl.
| | |
|---|---|
| *A61K 38/19* | (2006.01) |
| *C07K 14/765* | (2006.01) |
| *C07K 14/52* | (2006.01) |
| *C07K 14/00* | (2006.01) |
| *A61K 38/38* | (2006.01) |

(52) U.S. Cl.
CPC ................ *A61K 38/19* (2013.01); *A61K 38/385* (2013.01); *C07K 14/00* (2013.01); *C07K 14/52* (2013.01); *C07K 14/765* (2013.01); *C07K 2319/31* (2013.01)

(58) Field of Classification Search
CPC ..... A61K 38/19; A61K 38/385; C07K 14/52; C07K 14/765; C07K 2319/31
See application file for complete search history.

(56) References Cited

U.S. PATENT DOCUMENTS

| | | |
|---|---|---|
| 2004/0063635 A1 | 4/2004 | Yu et al. |
| 2009/0004181 A1 | 1/2009 | Breit |

FOREIGN PATENT DOCUMENTS

| | | |
|---|---|---|
| WO | 0179271 A1 | 10/2001 |
| WO | 0179443 A2 | 10/2001 |
| WO | 2005099746 A1 | 10/2005 |
| WO | 2013113008 A1 | 8/2013 |
| WO | 2013148117 A1 | 10/2013 |
| WO | 2014120619 A2 | 8/2014 |

OTHER PUBLICATIONS

Arai R. et al., Design of the linkers which effectively separate domains of a bifunctional fusion protein, Protein Engineering, 2001, vol. 14, No. 8, pp. 529-532.
Bauskin A. R. et al., The propeptide of macrophage inhibitory cytokine (MIC-1), a TGF-beta superfamily member, acts as a quality control determinant for correctly folded MIC-1, The EMBO Journal, 2000, vol. 19, No. 10, pp. 2212-2220.
Bootcov M. R. et al., MIC-1, a novel macrophage inhibitory cytokine, is a divergent member of the TGF-b superfamily, Proceedings of the National Academy of Sciences, 1997, vol. 94, pp. 11514-11519.
Chen X. et al., Fusion protein linkers: property, design and functionality, Advanced Drug Delivery Reviews, 2012, vol. 65, No. 10, pp. 1357-1369.
Lu Z. et al., Change of body weight and macrophage inhibitory cytokine-1 during chemotherapy in advanced gastric cancer: what is their clinical significance?, Public Library of Science One, 2014, vol. 9, No. 2, p. e88553.

*Primary Examiner* — Christina Bradley
(74) *Attorney, Agent, or Firm* — Leon Y. Lum

(57) ABSTRACT

The invention relates to MIC-1 fusion proteins. More specifically it relates to compounds comprising fusion proteins comprising a MIC-1 protein or an analog thereof at the C-terminus of the fusion protein and a functional variant of human serum albumin at the N-terminus of the fusion protein connected via a peptide linker. The compounds of the invention have MIC-1 activity. The invention also relates to pharmaceutical compositions comprising such compounds and pharmaceutically acceptable excipients, as well as the medical use of the compounds.

29 Claims, 1 Drawing Sheet

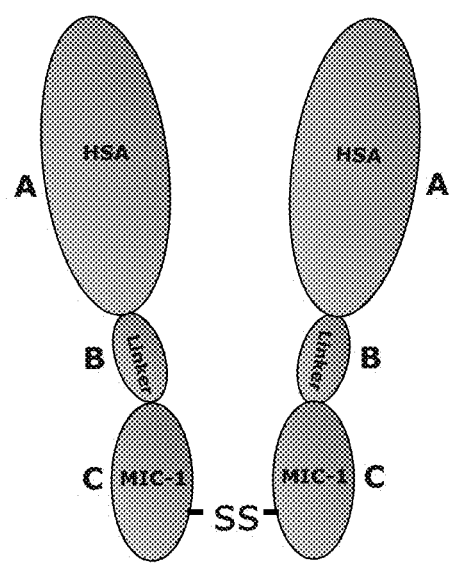

MIC-1 FUSION PROTEINS AND USES THEREOF

CROSS-REFERENCE TO RELATED APPLICATIONS

This application claims priority under 35 U.S.C. §119 to European Patent Application 14173664.5, filed Jun. 24, 2014; the contents of which is incorporated herein by reference.

TECHNICAL FIELD

The present invention relates to MIC-1 fusion proteins and their pharmaceutical use.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Sep. 21, 2015, is named 140026US01Seq_List_ST25.txt and is 28,566 bytes in size.

BACKGROUND

The macrophage inhibitory cytokine-1 (MIC-1), also known as GDF-15 and placental bone morphogenetic protein (PLAB), is a distant member of the TGF-beta super family, a family of peptide hormones involved in cell growth and differentiation. MIC-1 circulates as a cysteine-rich homodimer with a molecular mass of 24.5 kDa. MIC-1 was initially reported to be up-regulated in macrophages by stimuli including IL-1b, TNF-alpha, IL-2, and TGF-b. It was also shown that MIC-1 could reduce lipopolysaccharide-induced TNF-alpha production and it was based on these data proposed that MIC-1 was an anti-inflammatory cytokine. More recently, a study was investigating why human patients with advanced cancer were losing body weight and they showed that the weight loss correlated with circulating levels of MIC-1. These data indicates that MIC-1 regulates body weight. This hypothesis was tested in mice xenografted with prostate tumor cells, where data showed that elevated MIC-1 levels were associated with loss of body weight and decreased food intake, this effect being reversed by administration of antibodies to MIC-1. As administration of recombinant MIC-1 to mice regulated hypothalamic neuropeptide Y and pro-opiomelanocortin it was proposed that MIC-1 regulates food intake by a central mechanism. Furthermore, transgenic mice overexpressing MIC-1 are gaining less weight and body fat both on a normal low fat diet and on a high fat diet. Also, transgenic mice overexpressing MIC-1 fed both on a low and high fat diet, respectively, had improved glucose tolerance compared with wild type animals on a comparable diet.

Native MIC-1 has a short half-life, meaning that treatment with native MIC-1 requires daily administration to maintain efficacy.

WO 2001079443 concerns the use of human serum albumin or variants thereof for fusions to peptides of pharmaceutical interest.

WO 2005099746 concerns a method of modulating appetite and/or body weight by administering a MIC-1 modulating agent.

SUMMARY

The invention relates to MIC-1 fusion proteins.

In one aspect, the invention provides compounds comprising fusion proteins comprising a MIC-1 protein or an analogue thereof at the C-terminus of the fusion protein and a functional variant of human serum albumin (HSA) at the N-terminus of the fusion protein connected via a peptide linker. The peptide linker has a length of 10 to 50 amino acids and comprises the amino acid sequence $[X—Y_m]_n$, wherein X is Asp or Glu; Y is Ala; m is from 2 to 4, and n is at least 2.

In one aspect of the invention, Y is selected from the group of coded amino acids except for Pro and Gly. In another aspect, Y is selected from the group of coded non-polar amino acids, except for Pro and Gly.

In one aspect, the invention provides a polynucleotide molecule encoding a compound comprising a fusion protein comprising a MIC-1 protein or an analogue thereof at the C-terminus of the fusion protein and a functional variant of HUMAN SERUM ALBUMIN at the N-terminus of the fusion protein connected via a peptide linker.

In one aspect, the invention provides a pharmaceutical composition comprising a compound of the invention or a pharmaceutically acceptable salt, amide or ester thereof, and one or more pharmaceutically acceptable excipients.

In one aspect, the invention provides a compound of the invention for use as a medicament.

In one aspect, the invention provides a compound of the invention for use in the treatment of eating disorders, such as obesity, e.g. by decreasing food intake, reducing body weight, suppressing appetite and inducing satiety.

In one aspect, the invention provides a compound of the invention for use in the treatment of obesity.

In one aspect, the compounds of the invention are MIC-1 agonists. In one aspect, the compounds of the invention inhibit food intake. In one aspect, the compounds of the invention reduce body weight.

In one aspect, the compounds of the invention have longer half-life than the half-life of native MIC-1.

BRIEF DESCRIPTION OF DRAWINGS

FIG. 1. Schematic representation of a HSA-MIC-1 dimeric fusion protein. A, B and C depicts relative positions of the human serum albumin domain, the linker region and MIC-1, respectively. —SS— indicates interchain disulphide bridge linking together the two HSA-MIC-1 monomers to form a functional dimeric fusion protein.

DESCRIPTION

The invention relates to compounds comprising MIC-1 fusion proteins. In one aspect, the invention relates to MIC-1 fusion proteins.

In one aspect, the invention provides compounds comprising fusion proteins comprising MIC-1 or an analogue thereof at the C-terminus of the fusion protein and human serum albumin (HSA) or a functional variant thereof at the N-terminus of the fusion protein connected via a peptide linker. The peptide linker has a length of 10 to 50 amino acids and comprises the amino acid sequence $[X—Y_m]_n$, wherein X is Asp or Glu; Y is Ala; m is from 2 to 4, and n is at least 2.

In one aspect of the invention, Y is selected from the group of coded amino acids except for Pro and Gly. In another aspect, Y is selected from the group of coded non-polar amino acids, except for Pro and Gly.

The fusion protein strategy of the present invention combines the soluble, stable plasma protein human serum albumin with native MIC-1 or a MIC-1 analogue. Human serum albumin has inherent properties such as high solubility and stability which makes it beneficial to use as fusion partner for improving expression yield and conferring stability to MIC- 1. Human serum albumin as fusion partner may also increase the plasma half-life of MIC-1 by significant size increase, which inhibits renal clearance and/or by binding the Fc Neonatal Receptor, which allows recycling from the endosome and prevention of lysomal degradation allowing the molecule to be present longer in circulation. As with other smaller therapeutic proteins, native MIC-1 disappears rapidly from the bloodstream due to a short plasma half-life, meaning that treatment with native MIC-1 requires daily administration to maintain efficacy. The present invention provides compounds comprising MIC-1 fusion proteins with increased plasma half-life.

In what follows, Greek letters may be represented by their symbol or the corresponding written name, for example: α=alpha; β=beta; ϵ=epsilon; γ=gamma; ω=omega; etc. Also, the Greek letter of μ may be represented by "u", e.g. in μl=ul, or in μM=uM.

MIC-1 Proteins and Analogues

The term "MIC-1" as used herein means macrophage inhibitory cytokine-1 (MIC-1), also known as Growth Differentiation Factor 15 (GDF-15), and placental bone morphogenetic protein (PLAB). The sequence of the full length wild type human MIC-1 protein is available from the UNIPROT database with accession no. Q99988. The 308 amino acid precursor protein includes a signal peptide (amino acids 1-29), a propeptide (amino acids 30-196) and a mature protein (amino acids 197-308). The 112 amino acid mature MIC-1 protein is included herein as SEQ ID NO:1. Mature MIC-1 contains nine cysteine residues which give rise to the formation of 4 intrachain disulphide bonds and one interchain disulphide bond to create a covalently linked 24.5 kDa homodimer. A naturally occurring mutation corresponding to His6Asp in the mature protein (SEQ ID NO:1) has been described.

Thus particular examples of wild type human MIC-1 are the mature MIC-1 protein of SEQ ID NO:1, SEQ ID NO:1 having the amino acid modification His6Asp, as well as any of these sequences preceded by the propeptide and/or signal peptide referred to above.

The term "MIC-1 protein" as used herein refers to the human MIC-1 protein of SEQ ID NO:1, or an analogue thereof. The protein having the sequence of SEQ ID NO:1 may also be designated "hMIC-1", "native" MIC-1 or "wild type" MIC-1.

The term "MIC-1 analogue", or "analogue of MIC-1 protein" as used herein refers to a protein, or a compound, which is a variant of the mature MIC-1 protein (SEQ ID NO:1). In one aspect, the MIC-1 analogue is a functional variant of the mature MIC-1 protein (SEQ ID NO:1). In one aspect of the invention, the MIC-1 analogues display at least 85%, 90% or 95% sequence identity to native MIC-1 (SEQ ID NO:1).

In another aspect of the invention, the MIC-1 analogues comprise less than 17 amino acid modifications (substitutions, deletions, additions (including insertions) and any combination thereof) relative to human native MIC-1 (SEQ ID NO:1).). As an example of a method for determination of the sequence identity between two analogues the two peptides His6Asp MIC-1 and native MIC-1 are aligned. The sequence identity of the His6Asp MIC-1 analogue relative to native MIC-1 is given by the number of aligned identical residues minus the number of different residues divided by the total number of residues in native MIC-1. Accordingly, in said example the sequence identity in percentage is (112−1)/112×100.

The term "amino acid modification" used throughout this application is used in the meaning of a modification to an amino acid as compared to native MIC-1 (SEQ ID NO:1). This modification can be the result of a deletion of an amino acid, addition of an amino acid, substitution of one amino acid with another or a substituent covalently attached to an amino acid of the peptide.

Substitutions.

In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids.

In one aspect amino acids may be substituted by non-conservative substitution. The term "non-conservative substitution" as used herein denotes that one or more amino acids are replaced by another amino acid having different characteristics. Examples include substitution of a basic amino acid residue with an acidic amino acid residue, substitution of a polar amino acid residue with an aromatic amino acid residue, etc. In one aspect, the non-conservative substitution is substitution of a coded amino acid to another coded amino acid having different characteristics. In one aspect, the MIC-1 analogues may comprise substitutions of one or more unnatural and/or non-amino acids, e.g., amino acid mimetics, into the sequence of MIC-1.

The asparagine residue in position 3 of human mature MIC-1 (SEQ ID NO:1) is chemically labile. In one aspect of the invention, the asparagine in the position corresponding to position 3 of human mature MIC-1 (SEQ ID NO:1) may be substituted to Ser, Asp, Glu, Ala, Pro, Thr, Gly, or Gln. In one aspect of the invention, the asparagine in the position corresponding to position 3 of human mature MIC-1 (SEQ ID NO:1) has been substituted to Ser. In another aspect of the invention, the asparagine in the position corresponding to position 3 of human mature MIC-1 (SEQ ID NO:1) has been substituted to Glu.

In one aspect of the invention, the arginine in the position corresponding to position 2 of human mature MIC-1 (SEQ ID NO:1) has been substituted to alanine.

In one aspect of the invention, the arginine in the position corresponding to position 2 of human mature MIC-1 (SEQ ID NO:1) has been substituted to alanine, and the asparagine in the position corresponding to position 3 of human mature MIC-1 (SEQ ID NO:1) has been substituted to Glu.

Deletions and Truncations.

In one aspect, the MIC-1 analogues of the invention may have one or more amino acid residues deleted from the amino acid sequence of human MIC-1, alone or in combination with one or more insertions or substitutions.

In one aspect, the three N-terminal amino acids of human mature MIC-1 (Ala1, Arg2, Asn3) may be deleted.

Insertions.

In one aspect, the MIC-1 analogues of the invention may have one or more amino acid residues inserted into the amino acid sequence of human MIC-1, alone or in combination with one or more deletions and/or substitutions.

In one aspect, the MIC-1 analogues of the invention may include insertions of one or more unnatural amino acids and/or non-amino acids into the sequence of MIC-1.

MIC-1 analogues may be described by reference to i) the number of the amino acid residue in the mature MIC-1 protein which corresponds to the amino acid residue which is changed (i.e., the corresponding position in native MIC-1), and to ii) the actual change. In other words, a MIC-1 analogue is a MIC-1 protein in which a number of amino acid residues have been changed when compared to native MIC-1 (SEQ ID NO: 1). These changes may represent, independently, one or more amino acid substitutions, additions, and/or deletions.

As is apparent from the above examples, amino acid residues may be identified by their full name, their one-letter code, and/or their three-letter code. These three ways are fully equivalent.

The term "protein", as e.g. used in the context of MIC-1 proteins, refers to a compound which comprises a series of amino acids interconnected by amide (or peptide) bonds.

Amino acids are molecules containing an amine group and a carboxylic acid group, and, optionally, one or more additional groups, often referred to as a side chain.

The term "amino acid" includes coded (or proteinogenic or natural) amino acids (amongst those the 20 standard amino acids), as well as non-coded (or non-proteinogenic or non-natural) amino acids. Coded amino acids are those which are naturally incorporated into proteins. The standard amino acids are those encoded by the genetic code. Non-coded amino acids are either not found in proteins, or not produced by standard cellular machinery (e.g., they may have been subject to post-translational modification). In what follows, all amino acids of the MIC-1 proteins for which the optical isomer is not stated is to be understood to mean the L-isomer (unless otherwise specified).

Human Serum Albumin

Human serum albumin (HSA) belongs to a family of globular proteins and is composed of 585 amino acids with an approximate molecular weight of 67 kDa. Albumin comprises three homologous domains that assemble to form a heart-shaped molecule. Albumin is water-soluble and soluble in concentrated salt solutions and is commonly found in blood plasma. Albumin is the most abundant protein of human blood plasma and its main function is to regulate the osmotic pressure of blood, transport hormones or fatty acid and buffer pH. The normal range of human serum albumin in adults is 35 to 50 g/L and human serum albumin accounts for 80-90% of all plasma protein. As human serum albumin is a natural carrier for exogenous ligands, it has a low risk of inducing toxicity and immunogenicity and human serum albumin extracted from human blood can be used for clinical purposes. The plasma half-life of human serum albumin is approximately 20 days. The long half-life of human serum albumin is caused in part by a pH-dependent recycling mediated by the neonatal Fc receptor (FcRn). FcRn is present in cells and on the surface of cells, which interacts with circulating blood, such as vascular endothelial cells.

Recombinant human serum albumin fusion proteins comprising a therapeutic protein of interest may be achieved by genetic manipulation, such that the DNA coding for human serum albumin, or a fragment thereof, is joined to the DNA encoding for the therapeutic protein. A suitable expression host is then transformed or transfected with the fused nucleotide sequences encoded on a suitable plasmid as to express the fusion protein. Human serum albumin as fusion partner is thought to increase the plasma half-life of therapeutic proteins through two biological mechanisms. The significant size increase inhibits renal clearance and the inherent ability of human serum albumin to bind the Fc Neonatal Receptor will allow recycling from the endosome and prevention of lysomal degradation altogether allowing the molecule to be present longer in circulation.

Albumin fusion proteins can be produced in expression systems on a commercial scale and with lower cost than for other methods of generating therapeutic proteins with long plasma half-lives.

It is known to the person skilled in the art that functional variants of human serum albumin can be designed, which have the same plasma half-life prolonging benefits as the wild-type (truncated and/or amino acid substituted functional variants). For an example domain III of human serum albumin has been shown to bind FcN to a high degree and it is possible to make variants comprising only this domain or combinations with other domains, with long half-lives or half-lives that are modified (eg. Albufuse Flex Technology, Novozymes).

The sequence of the wild-type mature human serum albumin is included herein as SEQ ID NO:2 and the sequence is annotated in the Uniprot database with the accession no: P02768. The present invention provides a human serum albumin fusion protein comprising, or alternatively consisting of, a biologically active MIC-1 protein or a variant thereof and a biologically active and/or therapeutically active fragment or variant of human serum albumin. In one aspect, the invention provides a human serum albumin fusion protein comprising, or alternatively consisting of, mature native MIC-1 and the mature native human serum albumin. In one aspect of the invention, the primary sequence of human serum albumin is modified. Non-limiting examples includes functional variants of human serum albumin comprising truncations or amino acid substitutions or deletions in human serum albumin, which do not interfere with the half-life extending effect of human serum albumin. Human serum albumin contains a single thiol group from an unpaired cysteine residue at position 34 in Domain I. Cys34 in human serum albumin provides antioxidant activity and constitutes the largest fraction of free thiol groups in the blood. Cys34-Cys34 disulfide linkage of two human serum albumin molecules has several disadvantages, which includes side reactions with other residues during preparation, low stability or structural changes, which promotes protein aggregation. Substitutions of Cys34 with other amino acids, such as Ala or Ser has been described previously (Mccurdy, T et. Al., Journal of Laboratory and Clinical Medicine, Volume 143, Issue 2, 2004, 115-124). The term "HSA C34A" refers to a human serum albumin (HSA) variant wherein the cysteine residue at position 34 of the wild type human serum albumin amino acid sequence has been replaced with alanine. Other ways of preventing dimerization and instability through unfavourable interaction of free Cys at position 34 includes truncation of the N-terminal of human serum albumin domain I or removal of the Cys residue from the sequence.

By "functional variant" as used herein is meant a chemical variant of a certain protein which retains substantially the same function as the original protein.

Fusion Proteins

"Fusion protein" as used herein is intended to mean a hybrid protein expressed by a nucleic acid molecule comprising nucleotide sequences of at least two genes. "Fusion protein" as used herein is also intended to mean covalent joining of at least two proteins and/or peptides. In one aspect, the fusion proteins of the invention comprise human serum albumin as fusion partner fused with native MIC-1 having an activity of pharmaceutical interest. Fusion proteins are often used for improving recombinant expression or stability of therapeutic proteins as well as for improved recovery and purification of such proteins from cell cultures and the like. Fusion proteins may comprise artificial sequences, e.g. a linker sequence.

"Fusion partner" as used herein is intended to mean a protein which is part of a fusion protein, i.e. one of the at least two proteins encompassed by the fusion protein.

In one embodiment of the invention the fusion partner comprises human serum albumin with an approximate molecular weight of 67 kDa (SEQ ID NO:2) or functional variants thereof, which is operatively linked to the N-terminal of MIC-1 (SEQ ID NO:1) or functional variants thereof with a molecular weight of approximately 12 kDa via an interdomain linker region consisting of amino acid sequences of different length, charges and/or structural motifs.

"Fusion tag" as used herein is intended to mean a protein sequence which is part of a fusion protein, i.e. one of the at least two proteins encompassed by the fusion protein and comprises a sequence which improves expression, solubilisation or purification of the fusion protein, e.g. a 6× Histidine tag (such as His6) or a solubilization domain (such as Thiol:disulfide interchange protein DsbC (DsbC), Maltose Binding Protein (MBP), or Thioredoxin (Trx)).

In one aspect of the invention, monomers of NH2-HSA-linker-MIC-1-COOH with a size of approximately 80 kDa, homodimerizes as the native molecule via interchain disulphide bridge between the two MIC-1 molecules to form an active HSA-MIC-1 fusion protein with a molecular weight of approximately 160-165 kDa (depicted as schematic drawing in FIG. 1).

Peptide Linker

The term "peptide linker" as used herein is intended to mean an amino acid sequence which is typically used to facilitate the function, folding or expression of fusion proteins.

Different exposure of the MIC-1 protein comprised in a fusion protein to its putative receptor, plasma half-life or overall fusion protein stability may be affected by differences in the linker sequence/structure of the fusion protein, which can cause changes in biological efficacy, plasma half-life or fusion protein stability.

The linkers from the present invention were designed with different predicted biophysical or structural properties comprising variations in length (variation of the linker length), and predicted secondary structure such as alpha-helical structure, rigid structure or flexible, random coil structures or charge. In the present invention the length of the linker was varied from 7 to 35 amino acids. The linker length may influence the potential interaction between the human serum albumin and MIC-1 domain by changing the possibility of steric hindrance provided by the fusion partner attached to the biological active MIC-1 domain. The steric hindrance may influence correct folding of the two domains of the fusion protein monomer, formation of the dimer, the interaction of the MIC-1 part with a putative receptor, or the linker itself may interact with either human serum albumin or MIC-1 and that both composition and length of the linker may in part influence the nature and extent of such interaction.

Functional Properties

Biological Activity—In Vivo Pharmacology

In one aspect the compounds of the invention are potent in vivo, which may be determined as is known in the art in any suitable animal model, as well as in clinical trials.

The non-obese Sprague Dawley rat is one example of a suitable animal model, and the changes in food intake may be determined in such rats in vivo, e.g. as described in Example 2.

In one aspect the compounds of the invention inhibits in vivo food intake in non-obese Sprague Dawley rats.

As an example, in a particular aspect of the invention, the maximum efficacy which is the greatest significant ($p<0.10$) reduction in 24 hour food intake recorded over 6-7 days at a dose of 4 nmol/kg should be more than 20%, preferably more than 30%. In another particular aspect of the invention, the maximum efficacy which is the greatest significant ($p<0.10$) reduction in 24 hour food intake recorded over 6-7 days at a dose of 4 nmol/kg should be at least 20%, preferably at least 30%.

As an example, in a particular aspect of the invention, the accumulated efficacy which is the sum of significant ($p<0.10$) reductions in 24 hour food intake compared with vehicle at a dose of 4 nmol/kg should be more than 50%, more preferably more than 70%, even more preferably more than 80%, or most preferably more than 100%.

As an example, in a particular aspect of the invention, the accumulated efficacy which is the sum of significant ($p<0.10$) reductions in 24 hour food intake compared with vehicle at a dose of 4 nmol/kg should be at least 50%, more preferably at least 70%, even more preferably at least 80%, or most preferably at least 100%.

Diet-Induced Obese (DIO) Sprague Dawley rats is another example of a suitable animal model, and the changes in food intake may be determined in such rats in vivo, e.g. as described in Example 3.

In one aspect the compounds of the invention inhibits in vivo food intake in DIO Sprague Dawley rats.

In one aspect of the invention, the maximum efficacy which is the greatest significant ($p<0.10$) reduction in 24 hour food intake recorded over 6-7 days at a dose of 4 nmol/kg is at least 50%, or preferably at least 60%.

In one aspect of the invention, the accumulated efficacy which is the sum of significant ($p<0.10$) reductions in 24 hour food intake compared with vehicle at a dose of 4 nmol/kg is at least 300%, more preferably at least 340%, or even more preferably at least 380%.

Biophysical Properties

In one aspect, the compounds of the invention have good biophysical properties. These properties include but are not limited to physical stability and/or solubility. These and other biophysical properties may be measured using standard methods known in the art. In a particular embodiment, these properties are improved as compared to native MIC-1 (SEQ ID NO:1). Increased biophysical stability of a fusion protein compared to native MIC-1 may be at least partly be owing to stabilizing effects of the fusion partner or the length or composition of the intervening amino acid linker inserted between the human serum albumin and MIC-1 sequence.

Production Processes

Fusion proteins such as those of the present invention may be produced by means of recombinant protein technology known to persons skilled in the art. In general, nucleic acid sequences encoding the proteins of interest or functional variants thereof are modified to encode the desired fusion protein. This modification includes the in-frame fusion of the nucleic acid sequences encoding the two or more proteins to be expressed as a fusion protein. Such a fusion protein can be with or without a linker peptide as well as the fusion protein fused to a fusion tag, e.g. a Histidine tag (such as His6) or a solubilization domain (such as DsbC, MBP or Trx). This modified sequence is then inserted into an expression vector, which is in turn transformed or transfected into the expression host cells.

The nucleic acid construct encoding the fusion protein may suitably be of genomic, cDNA or synthetic origin. Amino acid sequence alterations are accomplished by modification of the genetic code by well-known techniques.

The DNA sequence encoding the fusion protein is usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the fusion protein is operably linked to additional segments required for transcription of the DNA. The term, "operably linked" indicates that the segments are arranged so that they function in concert for their intended purposes, e.g. transcription initiates in a promoter and proceeds through the DNA sequence coding for the polypeptide until it terminates within a terminator.

Thus, expression vectors for use in expressing the fusion protein will comprise a promoter capable of initiating and directing the transcription of a cloned gene or cDNA. The promoter may be any DNA sequence, which shows transcriptional activity in the host cell of choice and may be derived from genes encoding proteins either homologous or heterologous to the host cell.

Additionally, expression vectors for expression of the fusion protein will also comprise a terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Expression of the fusion protein can be aimed for either intracellular expression in the cytosol of the host cell or be directed into the secretory pathway for extracellular expression into the growth medium.

Intracellular expression is the default pathway and requires an expression vector with a DNA sequence comprising a promoter followed by the DNA sequence encoding the fusion protein followed by a terminator.

To direct the fusion protein into the secretory pathway of the host cells, a secretory signal sequence (also known as signal peptide or a pre sequence) is needed as an N-terminal extension of the fusion protein. A DNA sequence encoding the signal peptide is joined to the 5' end of the DNA sequence encoding the fusion protein in the correct reading frame. The signal peptide may be that normally associated with the protein or may be from a gene encoding another secreted protein.

The procedures used to ligate the DNA sequences coding for the fusion protein, the promoter, the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N. Y., 1989).

The host cell into which the DNA sequence encoding the fusion protein is introduced may be any cell that is capable of expressing the fusion protein either intracellularly or extracellularly. The fusion protein may be produced by culturing a host cell containing a DNA sequence encoding the fusion protein and capable of expressing the fusion protein in a suitable nutrient medium under conditions permitting the expression of the fusion protein. Non-limiting examples of host cells suitable for expression of fusion proteins are: *Escherichia coli, Saccharomyces cerevisiae*, as well as human embryonic kidney (HEK), Baby Hamster Kidney (BHK) or Chinese hamster ovary (CHO) cell lines. If post-translational modifications are needed, suitable host cells include yeast, fungi, insects and higher eukaryotic cells such as mammalian cells.

Once the fusion protein has been expressed in a host organism it may be recovered and purified to the required quality by conventional techniques. Non-limiting examples of such conventional recovery and purification techniques are centrifugation, solubilization, filtration, precipitation, ion-exchange chromatography, immobilized metal affinity chromatography (IMAC), Reversed phase-High Performance Liquid Chromatography (RP-HPLC), gel-filtration and freeze drying.

Examples of recombinant expression and purification of fusion proteins may be found in e.g. Cordingley et al., 3. Virol. 1989, 63, pp 5037-5045, Birch et al., Protein Expr Purif., 1995, 6, pp 609-618 and in WO2008/043847.

Examples of microbial expression and purification of fusion proteins may be found in e.g. Chich et al, Anal. Biochem, 1995, 224, pp 245-249 and Xin et al., Protein Expr. Purif. 2002, 24, pp 530-538.

Specific examples of methods of preparing a number of the compounds of the invention are included in the experimental part.

Mode of Administration

The term "treatment" is meant to include both the prevention and minimization of the referenced disease, disorder, or condition (i.e., "treatment" refers to both prophylactic and therapeutic administration of a compound of the invention or composition comprising a compound of the invention unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

The amount of a compound of this invention to be administered, the determination of how frequently to administer a compound of this invention, and the election of which compound or compounds of this invention to administer, optionally together with another pharmaceutically active agent, is decided in consultation with a practitioner who is familiar with the treatment of obesity and related disorders.

Pharmaceutical Compositions

Pharmaceutical compositions comprising a compound of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

Combination Treatment

The treatment with a compound according to the present invention may also be combined with one or more pharmacologically active substances, e.g., selected from antiobesity agents, appetite regulating agents, and agents for the treatment and/or prevention of complications and disorders resulting from or associated with obesity.

Pharmaceutical Indications

In one aspect, the present invention relates to a compound of the invention, for use as a medicament.

In particular embodiments, the compound of the invention may be used for the following medical treatments:

(i) Prevention and/or treatment of eating disorders, such as obesity, e.g. by decreasing food intake, reducing body weight, suppressing appetite and inducing satiety.

(ii) Prevention and/or treatment of hyperglycemia and/or impaired glucose tolerance.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the MIC-1 fusion proteins of the invention for treatment or prevention of obesity. In some embodiments the subject suffering from obesity is human, such as an adult human or a pediatric human (including infants, children, and adolescents). Body mass index (BMI) is a measure of body fat based on height and weight. The formula for calculation is BMI=weight in kilograms/height in meters2. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the MIC-1 fusion proteins of the invention for treatment or prevention of overweight, optionally in the presence of at least one weight-related comorbidity.

In some embodiments the subject suffering from overweight is human, such as an adult human or a pediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the MIC-1 fusion proteins of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

Particular Embodiments

The invention is further described by the following non-limiting embodiments of the invention:

1. A compound comprising a fusion protein of formula (I):

$$A\text{-}B\text{—}C \quad (I),$$

wherein
A is human serum albumin or a functional variant thereof;
B is a peptide linker comprising the amino acid sequence $[X\text{—}Y_m]_n$, wherein X is Asp or Glu; Y is Ala; m is from 2 to 4; and n is at least 2; and
C is a MIC-1 protein or an analogue thereof, and
wherein the C-terminus of human serum albumin or a functional variant thereof is fused to the N-terminus of the peptide linker, and the C-terminus of the peptide linker is fused to the N-terminus of the MIC-1 protein or analogue thereof.

2. A compound consisting of a fusion protein of formula (I):

$$A\text{-}B\text{—}C \quad (I),$$

wherein
A is human serum albumin or a functional variant thereof;
B is a peptide linker comprising the amino acid sequence $[X\text{—}Y_m]_n$, wherein X is Asp or Glu; Y is Ala; m is from 2 to 4; and n is at least 2; and
C is a MIC-1 protein or an analogue thereof, and
wherein the C-terminus of human serum albumin or a functional variant thereof is fused to the N-terminus of the peptide linker, and the C-terminus of the peptide linker is fused to the N-terminus of the MIC-1 protein or analogue thereof.

3. A compound comprising a fusion protein of formula (I):

$$A\text{-}B\text{—}C \quad (I),$$

wherein
A is human serum albumin or a functional variant thereof;
B is a peptide linker, wherein the peptide linker is 10 to 50 amino acids in length and comprises the amino acid sequence $[X\text{—}Y_m]_n$, wherein X is Asp or Glu; Y is Ala; m is from 2 to 4; and n is at least 2; and
C is a MIC-1 protein or an analogue thereof, and
wherein the C-terminus of human serum albumin or a functional variant thereof is fused to the N-terminus of the peptide linker, and the C-terminus of the peptide linker is fused to the N-terminus of the MIC-1 protein or analogue thereof.

4. A compound consisting of a fusion protein of formula (I):

$$A\text{-}B\text{—}C \quad (I),$$

wherein
A is human serum albumin or a functional variant thereof;
B is a peptide linker, wherein the peptide linker is 10 to 50 amino acids in length and comprises the amino acid sequence

[X—Y$_m$]$_n$, wherein X is Asp or Glu; Y is Ala; m is from 2 to 4; and n is at least 2; and C is a MIC-1 protein or an analogue thereof, and wherein the C-terminus of human serum albumin or a functional variant thereof is fused to the N-terminus of the peptide linker, and the C-terminus of the peptide linker is fused to the N-terminus of the MIC-1 protein or analogue thereof.

5. A compound according to any one of the preceding embodiments, wherein the compound is a homodimer of two fusion proteins of formula (I):

   (I)

formed by an interchain disulphide bridge between the two MIC-1 proteins or analogues thereof.

6. A compound according to any one of the preceding embodiments, wherein the peptide linker is 10 to 35 amino acids in length.

7. A compound according to any one of the preceding embodiments, wherein the peptide linker is 15 to 25 amino acids in length.

8. A compound according to any one of the preceding embodiments, wherein the peptide linker is 20 to 25 amino acids in length.

8a. A compound according to any one of the preceding embodiments, wherein the peptide linker is 20 to 30 amino acids in length.

9. A compound according to any one of the preceding embodiments, wherein the peptide linker consists of a maximum of 35 amino acids.

10. A compound according to any one of the preceding embodiments, wherein the peptide linker consists of a maximum of 30 amino acids.

11. A compound according to any one of the preceding embodiments, wherein the peptide linker consists of a maximum of 25 amino acids.

12. A compound according to any one of the preceding embodiments, wherein the peptide linker comprises the amino acid sequence [X—Y$_m$]$_n$X, wherein X is Asp or Glu; Y is Ala; m is from 2 to 4; and n is at least 2.

13. A compound according to any one of the preceding embodiments, wherein the peptide linker has the amino acid sequence [X—Y$_m$]$_n$X, wherein X is Asp or Glu; Y is Ala; m is from 2 to 4; and n is at least 2.

14. A compound according to any one of the preceding embodiments, wherein the peptide linker has the amino acid sequence [X—Y$_m$]$_n$X, wherein X is Asp or Glu; Y is Ala; m is from 2 to 4; and n is at least 5.

15. A compound according to any one of the preceding embodiments, wherein the peptide linker has the amino acid sequence [X—Y$_m$]$_n$X, wherein X is Asp or Glu; Y is Ala; m is from 2 to 3; and n is at least 5.

16. A compound according to any one of the preceding embodiments, wherein the peptide linker comprises the amino acid sequence GGSS[X—Y$_m$]$_n$X, wherein X is Asp or Glu; Y is Ala; m is from 2 to 4; and n is at least 2 (wherein GGSS is SEQ ID NO: 40).

17. A compound according to any one of the preceding embodiments, wherein the peptide linker has the amino acid sequence GGSS[X—Y$_m$]$_n$X, wherein X is Asp or Glu; Y is Ala; m is from 2 to 4; and n is at least 2 (wherein GGSS is SEQ ID NO: 40).

18. A compound according to any one of the preceding embodiments, wherein the peptide linker has the amino acid sequence GGSS[X—Y$_m$]$_n$X, wherein X is Asp or Glu; Y is Ala; m is from 2 to 4; and n is at least 5 (wherein GGSS is SEQ ID NO: 40).

19. A compound according to any one of the preceding embodiments, wherein the peptide linker has the amino acid sequence GGSS[X—Y$_m$]$_n$X, wherein X is Asp or Glu; Y is Ala; m is from 2 to 3; and n is at least 5 (wherein GGSS is SEQ ID NO: 40).

20. A compound according to any one of the preceding embodiments, wherein the peptide linker has the amino acid sequence GGSS[X—Y$_m$]$_n$X, wherein X is Asp or Glu; Y is Ala; m is 2; and n is 5 or 6 (wherein GGSS is SEQ ID NO: 40).

21. A compound according to any one of the preceding embodiments, wherein the peptide linker has the amino acid sequence GGSS[X—Y$_m$]$_n$X, wherein X is Asp or Glu; Y is Ala; m is 2; and n is 6 (wherein GGSS is SEQ ID NO: 40).

22. A compound according to any one of the preceding embodiments, wherein X is Asp.

23. A compound according to any one of the preceding embodiments, wherein X is Glu.

24. A compound according to any one of the preceding embodiments, wherein m is 2 and n is 2, 4 or 6.

25. A compound according to any one of the preceding embodiments, wherein n is 2, 4 or 6.

26. A compound according to any one of the preceding embodiments, wherein n is 6.

27. A compound according to any one of the preceding embodiments, wherein m is 2.

27a. A compound according to any one of the preceding embodiments, wherein m is 3.

28. A compound according to any one of the preceding embodiments, wherein the peptide linker comprises (Glu-Ala-Ala)$_6$ (SEQ ID NO: 39).

29. A compound according to any one of the preceding embodiments, wherein the peptide linker is (Glu-Ala-Ala)$_6$ (SEQ ID NO: 39).

30. A compound according to any one of the preceding embodiments, wherein the peptide linker comprises (Glu-Ala-Ala)$_6$-Glu (SEQ ID NO: 11).

31. A compound according to any one of the preceding embodiments, wherein the peptide linker is (Glu-Ala-Ala)$_6$-Glu (SEQ ID NO: 11).

32. A compound according to any one of the preceding embodiments, wherein the peptide linker comprises Gly-Gly-Ser-Ser-(Glu-Ala-Ala)$_6$-Glu (SEQ ID NO: 9).

33. A compound according to any one of the preceding embodiments, wherein the peptide linker is Gly-Gly-Ser-Ser-(Glu-Ala-Ala)$_6$-Glu (SEQ ID NO: 9).

34. A compound according to any one of the preceding embodiments, wherein the peptide linker comprises (Glu-Ala-Ala)$_{10}$-Glu (SEQ ID NO: 12).

35. A compound according to any one of the preceding embodiments, wherein the peptide linker is (Glu-Ala-Ala)$_{10}$-Glu (SEQ ID NO: 12).

36. A compound according to any one of the preceding embodiments, wherein the peptide linker comprises Gly-Gly-Ser-Ser-(Glu-Ala-Ala)$_{10}$-Glu (SEQ ID NO: 13).

37. A compound according to any one of the preceding embodiments, wherein the peptide linker is Gly-Gly-Ser-Ser-(Glu-Ala-Ala)$_{10}$-Glu (SEQ ID NO: 13).

38. A compound according to any one of the preceding embodiments, wherein the peptide linker comprises (Glu-Ala-Ala-Ala)$_5$-Glu (SEQ ID NO: 33).

39. A compound according to any one of the preceding embodiments, wherein the peptide linker is (Glu-Ala-Ala-Ala)$_5$-Glu (SEQ ID NO: 33).

40. A compound according to any one of the preceding embodiments, wherein the peptide linker comprises Gly-Gly-Ser-Ser-(Glu-Ala-Ala-Ala)$_5$-Glu (SEQ ID NO: 35).

41. A compound according to any one of the preceding embodiments, wherein the peptide linker is Gly-Gly-Ser-Ser-(Glu-Ala-Ala-Ala)$_5$-Glu (SEQ ID NO: 35).
42. A compound according to any one of the preceding embodiments, wherein the peptide linker comprises (Glu-Ala-Ala-Ala)$_6$-Glu (SEQ ID NO: 36).
43. A compound according to any one of the preceding embodiments, wherein the peptide linker is (Glu-Ala-Ala-Ala)$_6$-Glu (SEQ ID NO: 36).
44. A compound according to any one of the preceding embodiments, wherein the peptide linker comprises Gly-Gly-Ser-Ser-(Glu-Ala-Ala-Ala)$_6$-Glu (SEQ ID NO: 38).
45. A compound according to any one of the preceding embodiments, wherein the peptide linker is Gly-Gly-Ser-Ser-(Glu-Ala-Ala-Ala)$_6$-Glu (SEQ ID NO: 38).
46. A compound according to any one of the preceding embodiments, wherein the peptide linker comprises (Asp-Ala-Ala)$_6$-Asp (SEQ ID NO: 10).
47. A compound according to any one of the preceding embodiments, wherein the peptide linker is (Asp-Ala-Ala)$_6$-Asp (SEQ ID NO: 10).
48. A compound according to any one of the preceding embodiments, wherein the peptide linker comprises (Asp-Ala-Ala-Ala)$_5$-Asp (SEQ ID NO: 34).
49. A compound according to any one of the preceding embodiments, wherein the peptide linker is (Asp-Ala-Ala-Ala)$_5$-Asp (SEQ ID NO: 34).
50. A compound according to any one of the preceding embodiments, wherein the peptide linker comprises (Asp-Ala-Ala-Ala)$_6$-Asp (SEQ ID NO: 37).
51. A compound according to any one of the preceding embodiments, wherein C is an analogue of MIC-1 displaying at least 85% sequence identity to native MIC-1 (SEQ ID NO:1).
52. A compound according to any one of the preceding embodiments, wherein C is an analogue of MIC-1 displaying at least 90% sequence identity to native MIC-1 (SEQ ID NO:1).
53. A compound according to any one of the preceding embodiments, wherein C is an analogue of MIC-1 displaying at least 95% sequence identity to native MIC-1 (SEQ ID NO:1).
54. A compound according to any one of the preceding embodiments, wherein C is an analogue of MIC-1 having a maximum of 17 amino acid modifications compared to native MIC-1 (SEQ ID NO:1).
55. A compound according to any one of the preceding embodiments, wherein C is an analogue of MIC-1 having a maximum of 11 amino acid modifications compared to native MIC-1 (SEQ ID NO:1).
56. A compound according to any one of the preceding embodiments, wherein C is an analogue of MIC-1 having a maximum of 5 amino acid modifications compared to native MIC-1 (SEQ ID NO:1).
57. A compound according to any one of the preceding embodiments, wherein C is mature human MIC-1 (SEQ ID NO:1).
58. A compound according to any one of the preceding embodiments, wherein C is N3S hMIC-1 of SEQ ID NO:14.
59. A compound according to any one of the preceding embodiments, wherein C is R2A, N3E hMIC-1 of SEQ ID NO:15.
60. A compound according to any one of the preceding embodiments, wherein C is N3E hMIC-1 of SEQ ID NO:16.
61. A compound according to any one of the preceding embodiments, wherein C is N3A hMIC-1 of SEQ ID NO:17.
62. A compound according to any one of the preceding embodiments, wherein C is N3P hMIC-1 of SEQ ID NO:18.
63. A compound according to any one of the preceding embodiments, wherein C is N3T hMIC-1 of SEQ ID NO:19.
64. A compound according to any one of the preceding embodiments, wherein C is N3G hMIC-1 of SEQ ID NO:20.
65. A compound according to any one of the preceding embodiments, wherein C is N3Q hMIC-1 of SEQ ID NO:21.
66. A compound according to any one of the preceding embodiments, wherein C is N3D hMIC-1 of SEQ ID NO:22.
67. A compound according to any one of the preceding embodiments, wherein C is SEQ ID NO:14.
68. A compound according to any one of the preceding embodiments, wherein C is SEQ ID NO:15.
69. A compound according to any one of the preceding embodiments, wherein C is SEQ ID NO:16.
70. A compound according to any one of the preceding embodiments, wherein C is SEQ ID NO:17.
71. A compound according to any one of the preceding embodiments, wherein C is SEQ ID NO:18.
72. A compound according to any one of the preceding embodiments, wherein C is SEQ ID NO:19.
73. A compound according to any one of the preceding embodiments, wherein C is SEQ ID NO:20.
74. A compound according to any one of the preceding embodiments, wherein C is SEQ ID NO:21.
75. A compound according to any one of the preceding embodiments, wherein C is SEQ ID NO:22.
76. A compound according to any one of the preceding embodiments, wherein A is wild type human serum albumin of SEQ ID NO:2.
77. A compound according to any one of the preceding embodiments, wherein A is an analogue of human serum albumin displaying at least 85% sequence identity to wild type human serum albumin of SEQ ID NO:2.
78. A compound according to any one of the preceding embodiments, wherein A is an analogue of human serum albumin displaying at least 90% sequence identity to wild type human serum albumin of SEQ ID NO:2.
79. A compound according to any one of the preceding embodiments, wherein A is an analogue of human serum albumin displaying at least 95% sequence identity to wild type human serum albumin of SEQ ID NO:2.
80. A compound according to any one of the preceding embodiments, wherein A is C34A human serum albumin of SEQ ID NO:23.
81. A compound according to any one of the preceding embodiments, wherein A is SEQ ID NO:23.
82. A compound according to any one of the preceding embodiments, further comprising a fusion partner.
83. A compound according to any one of the preceding embodiments, further comprising an N-terminal fusion partner.
84. A compound according to any one of the preceding embodiments, wherein said compound is a MIC-1 agonist.
85. A compound according to any one of the preceding embodiments, wherein said compound is capable of decreasing food intake.
86. A compound according to any one of the preceding embodiments, wherein said compound has the effect in vivo of decreasing food intake determined in a single-dose study in non-obese Sprague Dawley rats.
87. A compound according to embodiment 1, consisting of a fusion protein of formula (I):

A-B—C (I), selected from the following:

A is human serum albumin protein of SEQ ID NO:2, B is the peptide linker of SEQ ID NO:10, and C is native human MIC-1 of SEQ ID NO:1;
A is human serum albumin protein of SEQ ID NO:2, B is the peptide linker of SEQ ID NO:11, and C is native human MIC-1 of SEQ ID NO:1;
A is human serum albumin protein of SEQ ID NO:2, B is the peptide linker of SEQ ID NO:33, and C is native human MIC-1 of SEQ ID NO:1;
A is human serum albumin protein of SEQ ID NO:2, B is the peptide linker of SEQ ID NO:34, and C is native human MIC-1 of SEQ ID NO:1;
A is human serum albumin protein of SEQ ID NO:2, B is the peptide linker of SEQ ID NO:9, and C is native human MIC-1 of SEQ ID NO:1;
A is human serum albumin protein of SEQ ID NO:2, B is the peptide linker of SEQ ID NO:35, and C is native human MIC-1 of SEQ ID NO:1;
A is human serum albumin protein of SEQ ID NO:2, B is the peptide linker of SEQ ID NO:36, and C is native human MIC-1 of SEQ ID NO:1;
A is human serum albumin protein of SEQ ID NO:2, B is the peptide linker of SEQ ID NO:37, and C is native human MIC-1 of SEQ ID NO:1;
A is human serum albumin protein of SEQ ID NO:2, B is the peptide linker of SEQ ID NO:38, and C is native human MIC-1 of SEQ ID NO:1;
A is human serum albumin protein of SEQ ID NO:2, B is the peptide linker of SEQ ID NO:12, and C is native human MIC-1 of SEQ ID NO:1;
A is human serum albumin protein of SEQ ID NO:2, B is the peptide linker of SEQ ID NO:13, and C is native human MIC-1 of SEQ ID NO:1;
A is human serum albumin protein of SEQ ID NO:23, B is the peptide linker of SEQ ID NO:9, and C is native human MIC-1 of SEQ ID NO:1;
A is human serum albumin protein of SEQ ID NO:23, B is the peptide linker of SEQ ID NO:9, and C is the MIC-1 variant of SEQ ID NO:14;
A is human serum albumin protein of SEQ ID NO:23, B is the peptide linker of SEQ ID NO:9, and C is the MIC-1 variant of SEQ ID NO:15;
A is human serum albumin protein of SEQ ID NO:23, B is the peptide linker of SEQ ID NO:9, and C is the MIC-1 variant of SEQ ID NO:16;
A is human serum albumin protein of SEQ ID NO:23, B is the peptide linker of SEQ ID NO:9, and C is the MIC-1 variant of SEQ ID NO:17;
A is human serum albumin protein of SEQ ID NO:23, B is the peptide linker of SEQ ID NO:9, and C is the MIC-1 variant of SEQ ID NO:18;
A is human serum albumin protein of SEQ ID NO:23, B is the peptide linker of SEQ ID NO:9, and C is the MIC-1 variant of SEQ ID NO:19;
A is human serum albumin protein of SEQ ID NO:23, B is the peptide linker of SEQ ID NO:9, and C is the MIC-1 variant of SEQ ID NO:20;
A is human serum albumin protein of SEQ ID NO:23, B is the peptide linker of SEQ ID NO:9, and C is the MIC-1 variant of SEQ ID NO:21; and
A is human serum albumin protein of SEQ ID NO:23, B is the peptide linker of SEQ ID NO:9, and C is the MIC-1 variant of SEQ ID NO:22.

88. A compound according to embodiment 1, consisting of a fusion protein of formula (I):

$$A\text{-}B\text{---}C \qquad (I),$$

selected from the following:
A is human serum albumin protein of SEQ ID NO:2, B is the peptide linker of SEQ ID NO:9, and C is native human MIC-1 of SEQ ID NO:1;
A is human serum albumin protein of SEQ ID NO:23, B is the peptide linker of SEQ ID NO:9, and C is native human MIC-1 of SEQ ID NO:1;
A is human serum albumin protein of SEQ ID NO:23, B is the peptide linker of SEQ ID NO:9, and C is the MIC-1 variant of SEQ ID NO:14; and
A is human serum albumin protein of SEQ ID NO:23, B is the peptide linker of SEQ ID NO:9, and C is the MIC-1 variant of SEQ ID NO:15.

89. A compound according to embodiment 1, wherein A is human serum albumin protein of SEQ ID NO:2, B is the peptide linker of SEQ ID NO:10, and C is native human MIC-1 of SEQ ID NO:1.

90. A compound according to embodiment 1, wherein A is human serum albumin protein of SEQ ID NO:2, B is the peptide linker of SEQ ID NO:11, and C is native human MIC-1 of SEQ ID NO:1.

91. A compound according to embodiment 1, wherein A is human serum albumin protein of SEQ ID NO:2, B is the peptide linker of SEQ ID NO:33, and C is native human MIC-1 of SEQ ID NO:1.

92. A compound according to embodiment 1, wherein A is human serum albumin protein of SEQ ID NO:2, B is the peptide linker of SEQ ID NO:34, and C is native human MIC-1 of SEQ ID NO:1.

93. A compound according to embodiment 1, wherein A is human serum albumin protein of SEQ ID NO:2, B is the peptide linker of SEQ ID NO:9, and C is native human MIC-1 of SEQ ID NO:1.

94. A compound according to embodiment 1, wherein A is human serum albumin protein of SEQ ID NO:2, B is the peptide linker of SEQ ID NO:35, and C is native human MIC-1 of SEQ ID NO:1.

95. A compound according to embodiment 1, wherein A is human serum albumin protein of SEQ ID NO:2, B is the peptide linker of SEQ ID NO:36, and C is native human MIC-1 of SEQ ID NO:1.

96. A compound according to embodiment 1, wherein A is human serum albumin protein of SEQ ID NO:2, B is the peptide linker of SEQ ID NO:37, and C is native human MIC-1 of SEQ ID NO:1.

97. A compound according to embodiment 1, wherein A is human serum albumin protein of SEQ ID NO:2, B is the peptide linker of SEQ ID NO:38, and C is native human MIC-1 of SEQ ID NO:1.

98. A compound according to embodiment 1, wherein A is human serum albumin protein of SEQ ID NO:2, B is the peptide linker of SEQ ID NO:12, and C is native human MIC-1 of SEQ ID NO:1.

99. A compound according to embodiment 1, wherein A is human serum albumin protein of SEQ ID NO:2, B is the peptide linker of SEQ ID NO:13, and C is native human MIC-1 of SEQ ID NO:1.

100. A compound according to embodiment 1, wherein A is human serum albumin protein of SEQ ID NO:23, B is the peptide linker of SEQ ID NO:9, and C is native human MIC-1 of SEQ ID NO:1.

101. A compound according to embodiment 1, wherein A is human serum albumin protein of SEQ ID NO:23, B is the peptide linker of SEQ ID NO:9, and C is the MIC-1 variant of SEQ ID NO:14.
102. A compound according to embodiment 1, wherein A is human serum albumin protein of SEQ ID NO:23, B is the peptide linker of SEQ ID NO:9, and C is the MIC-1 variant of SEQ ID NO:15.
103. A compound according to embodiment 1, wherein A is human serum albumin protein of SEQ ID NO:23, B is the peptide linker of SEQ ID NO:9, and C is the MIC-1 variant of SEQ ID NO:16.
104. A compound according to embodiment 1, wherein A is human serum albumin protein of SEQ ID NO:23, B is the peptide linker of SEQ ID NO:9, and C is the MIC-1 variant of SEQ ID NO:17.
105. A compound according to embodiment 1, wherein A is human serum albumin protein of SEQ ID NO:23, B is the peptide linker of SEQ ID NO:9, and C is the MIC-1 variant of SEQ ID NO:18.
106. A compound according to embodiment 1, wherein A is human serum albumin protein of SEQ ID NO:23, B is the peptide linker of SEQ ID NO:9, and C is the MIC-1 variant of SEQ ID NO:19.
107. A compound according to embodiment 1, wherein A is human serum albumin protein of SEQ ID NO:23, B is the peptide linker of SEQ ID NO:9, and C is the MIC-1 variant of SEQ ID NO:20.
108. A compound according to embodiment 1, wherein A is human serum albumin protein of SEQ ID NO:23, B is the peptide linker of SEQ ID NO:9, and C is the MIC-1 variant of SEQ ID NO:21.
109. A compound according to embodiment 1, wherein A is human serum albumin protein of SEQ ID NO:23, B is the peptide linker of SEQ ID NO:9, and C is the MIC-1 variant of SEQ ID NO:22.
110. A compound according to embodiment 1, consisting of a fusion protein of formula (I):

A-B—C          (I), wherein A is human serum albumin protein of SEQ ID NO:2, B is the peptide linker of SEQ ID NO:10, and C is native human MIC-1 of SEQ ID NO:1.
111. A compound according to embodiment 1, consisting of a fusion protein of formula (I):

A-B—C          (I), wherein A is human serum albumin protein of SEQ ID NO:2, B is the peptide linker of SEQ ID NO:11, and C is native human MIC-1 of SEQ ID NO:1.
112. A compound according to embodiment 1, consisting of a fusion protein of formula (I):

A-B—C          (I), wherein A is human serum albumin protein of SEQ ID NO:2, B is the peptide linker of SEQ ID NO:33, and C is native human MIC-1 of SEQ ID NO:1.
113. A compound according to embodiment 1, consisting of a fusion protein of formula (I):

A-B—C          (I), wherein A is human serum albumin protein of SEQ ID NO:2, B is the peptide linker of SEQ ID NO:34, and C is native human MIC-1 of SEQ ID NO:1.
114. A compound according to embodiment 1, consisting of a fusion protein of formula (I):

A-B—C          (I), wherein A is human serum albumin protein of SEQ ID NO:2, B is the peptide linker of SEQ ID NO:9, and C is native human MIC-1 of SEQ ID NO:1.
115. A compound according to embodiment 1, consisting of a fusion protein of formula (I):

A-B—C          (I), wherein A is human serum albumin protein of SEQ ID NO:2, B is the peptide linker of SEQ ID NO:35, and C is native human MIC-1 of SEQ ID NO:1.
116. A compound according to embodiment 1, consisting of a fusion protein of formula (I):

A-B—C          (I), wherein A is human serum albumin protein of SEQ ID NO:2, B is the peptide linker of SEQ ID NO:36, and C is native human MIC-1 of SEQ ID NO:1.
117. A compound according to embodiment 1, consisting of a fusion protein of formula (I):

A-B—C          (I), wherein A is human serum albumin protein of SEQ ID NO:2, B is the peptide linker of SEQ ID NO:37, and C is native human MIC-1 of SEQ ID NO:1.
118. A compound according to embodiment 1, consisting of a fusion protein of formula (I):

A-B—C          (I), wherein A is human serum albumin protein of SEQ ID NO:2, B is the peptide linker of SEQ ID NO:38, and C is native human MIC-1 of SEQ ID NO:1.
119. A compound according to embodiment 1, consisting of a fusion protein of formula (I):

A-B—C          (I), wherein A is human serum albumin protein of SEQ ID NO:2, B is the peptide linker of SEQ ID NO:12, and C is native human MIC-1 of SEQ ID NO:1.
120. A compound according to embodiment 1, consisting of a fusion protein of formula (I):

A-B—C          (I), wherein A is human serum albumin protein of SEQ ID NO:2, B is the peptide linker of SEQ ID NO:13, and C is native human MIC-1 of SEQ ID NO:1.
121. A compound according to embodiment 1, consisting of a fusion protein of formula (I):

A-B—C          (I), wherein A is human serum albumin protein of SEQ ID NO:23, B is the peptide linker of SEQ ID NO:9, and C is native human MIC-1 of SEQ ID NO:1.
122. A compound according to embodiment 1, consisting of a fusion protein of formula (I):

A-B—C          (I), wherein A is human serum albumin protein of SEQ ID NO:23, B is the peptide linker of SEQ ID NO:9, and C is the MIC-1 variant of SEQ ID NO:14.
123. A compound according to embodiment 1, consisting of a fusion protein of formula (I):

A-B—C          (I), wherein A is human serum albumin protein of SEQ ID NO:23, B is the peptide linker of SEQ ID NO:9, and C is the MIC-1 variant of SEQ ID NO:15.

124. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:16.

125. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:17.

126. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:18.

127. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:19.

128. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:20.

129. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:21.

130. A compound according to embodiment 1, consisting of a fusion protein of formula (I):

A-B—C    (I), wherein A is human serum albumin protein of SEQ ID NO:23, B is the peptide linker of SEQ ID NO:9, and C is the MIC-1 variant of SEQ ID NO:22.

131. A compound according to embodiment 1, selected from the following: compound 23, compound 24, and compound 26.

132. A compound according to embodiment 1, wherein the compound is compound 23.

133. A compound according to embodiment 1, wherein the compound is compound 24.

134. A compound according to embodiment 1, wherein the compound is compound 25.

135. A compound according to embodiment 1, wherein the compound is compound 26.

136. A compound according to embodiment 1, consisting of a His-tagged fusion protein of formula (I), wherein the His-tag is the His-tag of SEQ ID NO:3, A is human serum albumin protein of SEQ ID NO:2, B is the peptide linker of SEQ ID NO:9, and C is native human MIC-1 of SEQ ID NO:1.

137. A compound according to embodiment 1, consisting of a His-tagged fusion protein of formula (I), wherein the His-tag is the His-tag of SEQ ID NO:3, A is human serum albumin protein of SEQ ID NO:2, B is the peptide linker of SEQ ID NO:10, and C is native human MIC-1 of SEQ ID NO:1.

138. A compound according to embodiment 1, consisting of a His-tagged fusion protein of formula (I), wherein the His-tag is the His-tag of SEQ ID NO:3, wherein A is human serum albumin protein of SEQ ID NO:2, B is the peptide linker of SEQ ID NO:11, and C is native human MIC-1 of SEQ ID NO:1.

139. A compound according to embodiment 1, consisting of a His-tagged fusion protein of formula (I), wherein the His-tag is the His-tag of SEQ ID NO:3, wherein A is human serum albumin protein of SEQ ID NO:2, B is the peptide linker of SEQ ID NO:12, and C is native human MIC-1 of SEQ ID NO:1.

140. A compound according to embodiment 1, consisting of a His-tagged fusion protein of formula (I), wherein the His-tag is the His-tag of SEQ ID NO:3, wherein A is human serum albumin protein of SEQ ID NO:2, B is the peptide linker of SEQ ID NO:13, and C is native human MIC-1 of SEQ ID NO:1.

141. A pharmaceutical composition comprising a compound according to any one of embodiments 1-140 or a pharmaceutically acceptable salt, amide or ester thereof, and one or more pharmaceutically acceptable excipients.

142. A compound according to any one of embodiments 1-140 for use as a medicament.

143. A compound according to any one of embodiments 1-140 for use in the prevention and/or treatment of eating disorders, such as obesity, e.g. by decreasing food intake, reducing body weight, suppressing appetite and inducing satiety.

144. A compound according to any one of embodiments 1-140 for use in the prevention and/or treatment of obesity.

145. The use of a compound according to any one of embodiments 1-140 in the manufacture of a medicament for the treatment of eating disorders, such as obesity, e.g. by decreasing food intake, reducing body weight, suppressing appetite and inducing satiety.

146. The use of a compound according to any one of embodiments 1-140 in the manufacture of a medicament for the treatment of obesity.

147. A method of treating or preventing eating disorders, such as obesity, e.g. by decreasing food intake, reducing body weight, suppressing appetite and inducing satiety by administering a pharmaceutically active amount of a compound according to any one of embodiments 1-140.

148. A method of treating or preventing obesity by administering a pharmaceutically active amount of a compound according to any one of embodiments 1-140.

149. A polynucleotide molecule encoding a compound according to any one of embodiments 1-140.

EXAMPLES

This experimental part starts with a list of abbreviations, and is followed by a section including general methods of preparation, purification and characterisation of the compounds of the invention. Then follows an example relating to the activity and properties of these fusion proteins (section headed pharmacological methods). The examples serve to illustrate the invention.

List of Abbreviations

"Main peak" refers to the peak in a purification chromatogram which has the highest UV intensity in milliabsorbance units and which contains the fusion protein.

HPLC is High performance liquid chromatography.

SDS-PAGE is Sodium dodecyl sulfate Polyacrylamide gel electrophoresis.
IMAC is immobilized metal affinity chromatography.
SEC is size exclusion chromatography.
MS is mass spectrometry.
Materials and Methods
General Methods of Preparation
General Expression Method 1: Small Scale Screening and Expression of Fusion Constructs Expression levels for each construct were determined by transient transfection of the plasmids into Human Embryonic Kidney (HEK) cells (Expi293F™, Life Technologies™ #A14527) in 2 ml suspension cultures grown in Expi293™ Expression Medium (Life Technologies™ #A1435101). The expi293 cells were grown in disposable 24-well multiwell blocks (Axygen, #P-DW-10 ml-24-C-S) at 37° C., 8% $CO_2$ and 80% humidity. The shaking speed was 200 rpm in an Infors Multitron Cell incubator with a 50 mm orbital throw. For each transfection, 2 μg DNA in 100 ul of transfection medium (Opti-MEM® I (1×)+GlutaMAX™-I Reduced Serum Medium, Life Technologies™ #51985-026) and 5.4 μl ExpiFectamine™ 293 reagent (ExpiFectamine™ 293 Transfection Kit, Life Technologies™ #A14525) in transfection medium were used, according to the manufacturer's instructions. 18 hours after transfection, the cultures were fed with 10 μl enhancer 1 and 100 μl enhancer 2 (ExpiFectamine™ 293 Transfection Kit, Life Technologies™ #A14525). Approximately 90 hours after transfection, the cell cultures were harvested by centrifugation at 4000 g for 10 minutes, and the clarified culture medium used for further analysis of protein expression.

The relative expression levels of the constructs were determined by loading clarified cell supernatants directly on SDS-PAGE (Sodium dodecyl sulfate Polyacrylamide gel electrophoresis) gels (Novex® NuPAGE® 4-12% Bis-Tris midi protein gels, 26 wells, Life Technologies™ #WG1403BOX) without sample reduction, and the resulting protein bands visualized by Coomassie staining (InstantBlue™, Expedeon #ISBL1L). The production feasibility of each fusion protein was assessed by a small scale purification screen using an immobilized metal affinity chromatography (IMAC) step. The purified protein solutions were visualized by SDS-PAGE and Coomassie staining as described above and the results were used to determine the cell culture volume needed of each construct to provide enough protein for in vivo assessment of efficacy.

General Expression Method 2: Scale-Up Expression of his-Tagged HSA-MIC-1 Fusion Proteins The plasmids encoding MIC-1 fusion proteins were transformed to OneShot® Top10F' chemically competent E. coli cells (Life Technologies' #C303003), colonies were grown on Amp/Carb selective agar plates and transformants used to inoculate liquid Terrific Broth (TB) cultures. After overnight growth, the pelleted E. coli cells were used for large scale plasmid preparations (EndoFree® Plasmid Mega Kit, Qiagen® #12381).

Transient expression was performed by adding plasmid DNA (1 mg/liter cell culture) in OptiMEM® transfection medium (50 ml/liter cell culture) to ExpiFectamine™ 293 reagent (2.7 ml/liter cell culture) in OptiMEM® transfection medium (50 ml/liter cell culture), incubating for 20 minutes and then adding the transfection mix to the cell culture (expi293F cells at 3×106 cells/ml). 18 hours after transfection, the cultures were fed with enhancers 1 (5 ml/liter cell culture) and enhancer 2 (50 ml/liter cell culture). The expi293 cells were grown in 1 liter disposable shaker flasks (Corning #CLS431147) at 37° C., 8% $CO_2$ and 80% humidity. The shaking speed was 110 rpm in an Infors Multitron Cell incubator with a 50 mm orbital throw.

Approximately 90 hours after transfection the cultures were harvested by centrifugation at 4000 g for 10 minutes. The clarified medium was sterile filtered through a 0.22 uM filter before purification.

Purification

Following centrifugation and filtration through a 0.22 μm PES Bottle-top filter (Techno Plastic Products AG, Switzerland) the clarified supernatant was conditioned for IMAC purification by addition of 200 mL His-binding buffer (300 mM Sodium Phosphate (NaP), 1.8 M NaCl, 60 mM imidazole, pH 7.5) per liter supernatant.

Using an ÄKTAxpress chromatography system, the conditioned supernatant was applied at low flowrate to a 5 ml HisTrap Excel column (GE-Healthcare, Sweden) equilibrated in Buffer A (50 mM NaP, 300 mM NaCl, 10 mM Imidazole, pH 7.5) after which low affinity binding impurities were eluted with Wash Buffer (50 mM NaP, 300 mM NaCl, 30 mM Imidazole, pH 7.5). Bound fusion protein was step eluted with 100% Buffer B (50 mM NaP, 300 mM NaCl, 500 mM Imidazole, pH 7.5) and the main peak was collected using the peak detection option of the Unicorn™ software and automatically purified further using preparative size exclusion chromatography (SEC) in 1×PBS pH 7.4 (Ampliqon) on a HiLoad Superdex 200 16/600 PG column (GE-Healtcare, Sweden). 1.5 ml fractions were collected and analyzed by reducing and non-reducing SDS-PAGE using precast 4-12% NuPAGE® gels (Life Technologies™). In short the samples were mixed with 4×LDS (lithium dodecyl sulphate) sample buffer supplemented with 10× reducing agent when reduction was required. The mixture was heated 5 minutes at 95° C. before loading the SDS-PAGE gels. Novex SeeBlue® plus2 pre-stained Protein standard (Life Technologies™) were run alongside the fractions on SDS-PAGE for size estimation. Protein was visualized using InstantBlue™ stain (Expedeon, Cambridgeshire, UK) according to the manufacturer instructions.

General Expression Method 3: Recombinant Expression of HSA-Linker-MIC-1 Fusion Protein Generation of Vectors for Recombinant Expression of HSA-Linker-MIC-1 Fusion Proteins:

A series of CMV promoter-based expression vectors (pTT vectors) were generated for transient expression of HSA-linker-MIC-1 fusion proteins in EXPI293F cells (Life Technologies). The pTT vectors were generated for transient protein expression in the HEK293-6E EBNA-based expression system developed by Yves Durocher (Durocher et al. Nucleic Acid Research, 2002) and can be used for transient expression in the Expi293 expression system.

Initially, the gene constructs of each Albumin-linker-MIC-1 fusion protein variant were ordered in pTT vectors at Genscript with the human CD33 signal peptide sequence. The plasmids were subsequently transformed into E. coli for selection and the sequences of the constructs were verified by DNA sequencing.

Recombinant Expression of Fusion Proteins:

The HSA-linker-MIC-1 fusion proteins were expressed transiently in EXPI293F cells (Life 30 Technologies) by transfection of the pTT-based expression vectors according to manufacturer's instructions. The following procedure describes the generic EXPI293F expression protocol.

Cell Maintenance:

EXPI293F cells were grown in suspension in Expi293™ expression medium (Life Technologies). Cells were cultured in Erlenmeyer shaker flasks in an orbital shaker incubator at 36.5° C., 8% CO2 and 85-125 rpm and maintained at cell densities between 0.4-4×10E6 cells/mL.

DNA Transfection:

Typically, 30-1000 mL culture volumes were transfected. Separate dilutions of DNA and transfection reagent were initially prepared. Following components were mixed per 1-mL cell culture:

1. A total of 1 μg vector DNA was diluted in 50 μL Opti-MEM media (Gibco) and incubated at room temperature (23-25° C.) for 5 min.
2. A total of 2.7 μL Expifectamin™ 293 (Life Technologies) was diluted in 50 μL Opti-MEM media (Gibco) and incubated at room temperature (23-25° C.) for 5 min.

The two separate dilutions were mixed and incubated at room temperature (23-25° C.) for 10 min. The DNA-Expifectamin™ 293 mix was added directly to 1 mL EXPI293F cell culture. At the time of transfection the cell density of the EXPI293F culture should be 2.8-3.2×10E6 cells/mL. The transfected cell cultures were incubated in an orbital shaker incubator at 36.5° C., 8% CO2 and 85-125 rpm. 18 hrs post transfection; 5 uL Expifectamin™ 293 Transfection Enhancer 1 and 50 uL Expifectamin™ 293 Transfection Enhancer 2 were added per 1-mL culture. 5 days post transfection; the cell culture supernatants were harvested by centrifugation, followed by filtration through a 0.22 μm PES filter unit (Corning).

Purification

The fusion proteins were captured on a Gigacap column (ion exchange) at pH 8 (neutral pH) and eluted with an increase in salt (sodium sulphate) concentration using a stepwise gradient. The eluted protein was either concentrated on Amicon Ultra centrifugal filters with a MWCO of 10 kDa or not, depending on the concentration in the capture pool. The analogue was finally purified on a HiLoad Superdex200 16/60 or 26/60 prep grade column using a PBS buffer.

General Methods of Detection and Characterisation

MS Analysis

Intact mass of the purified combined fusion protein was analysed using Thermo-Dionex Ultimate3000™ HPLC (Thermo Fisher Scientific) coupled to a Maxis Impact™ ESI-Q-OTOF mass spectrometer (Bruker Daltonics). Solvents were A: Water with 0.1% Formic Acid (v/v) and B: Acetonitrile with 0.08% Formic acid (v/v). The sample was desalted online on a Waters Acquity™ BEH300 C4 1.7 μm 1.0×100 mm column (Waters) for 2 minutes in 10% B, 0.2 ml/min and eluted by a 8 minute linear gradient from 10% B to 90% B solvent at 0.2 ml/min.

Absorbance at 215 nm (Abs215) and m/z spectra in the range m/z 300 to 3000 were recorded. Obtained data was analysed using the DataAnalysis 4.1 software (Bruker Daltonics). Averaged m/z spectra were deconvoluted using Maximum Entropy deconvolution.

Peptide mass mapping was performed to verify correct linker sequences and was done using methods know to persons skilled in the art. In short, purified proteins were subjected to tryptic digestion using a method adopted from "In solution tryptic digest and guanidation kit", Pierce product nr. 89895. Peptide mass mapping to allow identification and verification of the correct linker linker sequence in the fusion proteins was done using the Data analysis software (Bruker Daltonics) to extract experimental determined masses of peptides and the Biotools software (Biotools) for matching experimental masses against the calculated masses derived from the expected fusion protein sequences according to the manufacturer's instructions. In general, variable modifications were set to "Oxidation (M)" and "Carbamidomethyl (C)" and the mass tolerance was set to 20 ppm and MS/MS tolerance to 50 mmu.

Chemiluminescent Nitrogen Detection (CLND) coupled to a standard HPLC was used to determine the protein concentration essentially as described elsewhere (eg. Bizanek, R.; Manes, 3. D.; Fujinari, E. M. Chemiluminescent nitrogen detection as a new technique for purity assessment of synthetic peptides separated by reversed-phase HPLC. Pept. Res. 1996, 9 (1), 40-44).

Example 1

Expression and Purification of the Compounds of the Invention

The different plasmids encoding the fusion protein variants depicted in Table 1 were designed with differences in the linker sequence between the human serum albumin part and the MIC-1 part.

TABLE 1

List of HSA MIC-1 fusion proteins. Compounds referred to in the table has human serum albumin or a human serum albumin variant in the N-terminal, a linker sequence as indicated with an amino acid sequence and wild type human MIC-1 or a MIC-1 functional variant in the C-terminal (see also FIG. 1). An N-terminal His6 tag (SEQ ID NO: 3) was included for some constructs to facilitate IMAC purification.

| Compound | N-terminal His-tag | Human serum sequence albumin (HSA) | Linker sequence | MIC-1 Protein | General expression method used | Peptide map (sequence coverage, %) |
|---|---|---|---|---|---|---|
| 1 | SEQ ID NO: 3 | SEQ ID NO: 2 | No linker | SEQ ID NO: 1 | 2 | 53.8 |
| 2 | SEQ ID NO: 3 | SEQ ID NO: 2 | SEQ ID NO: 4 | SEQ ID NO: 1 | 2 | 68.3 |
| 3 | SEQ ID NO: 3 | SEQ ID NO: 2 | SEQ ID NO: 5 | SEQ ID NO: 1 | 2 | 82.8 |
| 4 | SEQ ID NO: 3 | SEQ ID NO: 2 | SEQ ID NO: 6 | SEQ ID NO: 1 | 2 | 32.0 |
| 5 | SEQ ID NO: 3 | SEQ ID NO: 2 | SEQ ID NO: 10 | SEQ ID NO: 1 | 2 | 60.5 |
| 6 | SEQ ID NO: 3 | SEQ ID NO: 2 | SEQ ID NO: 8 | SEQ ID NO: 1 | 2 | 70.0 |
| 7 | SEQ ID NO: 3 | SEQ ID NO: 2 | SEQ ID NO: 9 | SEQ ID NO: 1 | 2 | 53.6 |

TABLE 1-continued

List of HSA MIC-1 fusion proteins. Compounds referred to in the table has
human serum albumin or a human serum albumin variant in the N-terminal, a linker
sequence as indicated with an amino acid sequence and wild type human MIC-1 or a
MIC-1 functional variant in the C-terminal (see also FIG. 1). An N-terminal His6 tag
(SEQ ID NO: 3) was included for some constructs to facilitate IMAC purification.

| Compound | N-terminal His-tag | Human serum sequence albumin (HSA) | Linker sequence | MIC-1 Protein | General expression method used | Peptide map (sequence coverage, %) |
|---|---|---|---|---|---|---|
| 8 | SEQ ID NO: 3 | SEQ ID NO: 2 | SEQ ID NO: 7 | SEQ ID NO: 1 | 2 | 62.9 |
| 9 | SEQ ID NO: 3 | SEQ ID NO: 2 | SEQ ID NO: 11 | SEQ ID NO: 1 | 2 | 69.5 |
| 10 | SEQ ID NO: 3 | SEQ ID NO: 2 | SEQ ID NO: 12 | SEQ ID NO: 1 | 2 | 66.3 |
| 11 | SEQ ID NO: 3 | SEQ ID NO: 2 | SEQ ID NO: 13 | SEQ ID NO: 1 | 2 | 71.6 |
| 12 | SEQ ID NO: 3 | SEQ ID NO: 2 | SEQ ID NO: 24 | SEQ ID NO: 1 | 2 | 49.4 |
| 13 | SEQ ID NO: 3 | SEQ ID NO: 2 | SEQ ID NO: 25 | SEQ ID NO: 1 | 2 | 62.5 |
| 14 | SEQ ID NO: 3 | SEQ ID NO: 2 | SEQ ID NO: 26 | SEQ ID NO: 1 | 2 | 64.1 |
| 15 | SEQ ID NO: 3 | SEQ ID NO: 2 | SEQ ID NO: 27 | SEQ ID NO: 1 | 2 | 75.5 |
| 16 | SEQ ID NO: 3 | SEQ ID NO: 2 | SEQ ID NO: 28 | SEQ ID NO: 1 | 2 | 64.8 |
| 17 | SEQ ID NO: 3 | SEQ ID NO: 2 | SEQ ID NO: 29 | SEQ ID NO: 1 | 2 | 31.0 |
| 18 | SEQ ID NO: 3 | SEQ ID NO: 2 | SEQ ID NO: 30 | SEQ ID NO: 1 | 2 | 73.1 |
| 19 | SEQ ID NO: 3 | SEQ ID NO: 2 | SEQ ID NO: 31 | SEQ ID NO: 1 | 2 | 84.7 |
| 20 | SEQ ID NO: 3 | SEQ ID NO: 2 | SEQ ID NO: 32 | SEQ ID NO: 1 | 2 | 78.3 |
| 21 | SEQ ID NO: 3 | SEQ ID NO: 2 | SEQ ID NO: 33 | SEQ ID NO: 1 | 2 | 74.0 |
| 22 | SEQ ID NO: 3 | SEQ ID NO: 2 | SEQ ID NO: 34 | SEQ ID NO: 1 | 2 | 81.8 |
| 23 | no His-tag | SEQ ID NO: 2 | SEQ ID NO: 9 | SEQ ID NO: 1 | 3 | 75.1 |
| 24 | no His-tag | SEQ ID NO: 23 | SEQ ID NO: 9 | SEQ ID NO: 1 | 3 | 79.3 |
| 25 | no His-tag | SEQ ID NO: 23 | SEQ ID NO: 9 | SEQ ID NO: 14 | 3 | 71.0 |
| 26 | no His-tag | SEQ ID NO: 23 | SEQ ID NO: 9 | SEQ ID NO: 15 | 3 | 73.8 |
| 27 | SEQ ID NO: 3 | SEQ ID NO: 23 | SEQ ID NO: 9 | SEQ ID NO: 16 | 2 | 87.0 |
| 28 | SEQ ID NO: 3 | SEQ ID NO: 23 | SEQ ID NO: 9 | SEQ ID NO: 17 | 2 | 86.5 |
| 29 | SEQ ID NO: 3 | SEQ ID NO: 23 | SEQ ID NO: 9 | SEQ ID NO: 18 | 2 | 84.3 |
| 30 | SEQ ID NO: 3 | SEQ ID NO: 23 | SEQ ID NO: 9 | SEQ ID NO: 19 | 2 | 82.2 |
| 31 | SEQ ID NO: 3 | SEQ ID NO: 23 | SEQ ID NO: 9 | SEQ ID NO: 20 | 2 | 91.1 |
| 32 | SEQ ID NO: 3 | SEQ ID NO: 23 | SEQ ID NO: 9 | SEQ ID NO: 21 | 2 | 83.6 |
| 33 | SEQ ID NO: 3 | SEQ ID NO: 2 | SEQ ID NO: 35 | SEQ ID NO: 1 | 2 | 62.6 |
| 34 | SEQ ID NO: 3 | SEQ ID NO: 2 | SEQ ID NO: 36 | SEQ ID NO: 1 | 2 | 75.1 |
| 35 | SEQ ID NO: 3 | SEQ ID NO: 2 | SEQ ID NO: 37 | SEQ ID NO: 1 | 2 | 79.6 |
| 36 | SEQ ID NO: 3 | SEQ ID NO: 2 | SEQ ID NO: 38 | SEQ ID NO: 1 | 2 | 74.1 |
| 37 | SEQ ID NO: 3 | SEQ ID NO: 23 | SEQ ID NO: 9 | SEQ ID NO: 22 | 2 | 76.4 |

Some fusion proteins comprise wild type human MIC-1 (SEQ ID NO:1), others MIC-1 variants (SEQ ID NO:14-SEQ ID NO:23). Some fusion proteins comprises human wild type human serum albumin (SEQ ID NO:2), others HSA C34A, a human serum albumin variant wherein the cysteine residue at position 34 of the wild type human serum albumin amino acid sequence has been replaced with alanine (SEQ ID NO:23). Plasmids were generated by well-known recombinant DNA technology methods (obtained from GenScript Inc). Constructs were designed with or without a N-terminal His tag sequence (SEQ ID NO:3). Constructs with His tag allows direct purification using immobilized affinity chromatography (IMAC), whereas other means of purification was used for purification of non-His tagged constructs. Since the His-tag is placed in the very N-terminal of human serum albumin it does not affect neither the efficacy of the MIC-1 fusion proteins, nor the binding of human serum albumin to Fc Neonatal Receptor and the half-life extending effect of human serum albumin, when used as a fusion partner. The linker sequence is given in Table 2.

TABLE 2

List of peptide linkers with corresponding SEQ ID NO and amino acid sequence.

| SEQ ID NO | Linker sequence |
| --- | --- |
| SEQ ID NO: 4 | EAAEAAE |
| SEQ ID NO: 5 | EEEAEEEAEEEAEEEAEEE |
| SEQ ID NO: 6 | GGSSSGSGGSGGSGSGGSGGSGS |
| SEQ ID NO: 7 | DDADDADDADDADDADDAD |
| SEQ ID NO: 8 | KAAKAAKAAKAAKAAKAAK |
| SEQ ID NO: 9 | GGSSEAAEAAEAAEAAEAAEAAE |
| SEQ ID NO: 10 | DAADAADAADAADAADAAD |
| SEQ ID NO: 11 | EAAEAAEAAEAAEAAEAAE |
| SEQ ID NO: 12 | EAAEAAEAAEAAEAAEAAEAAEAAEAAEAAE |
| SEQ ID NO: 13 | GGSSEAAEAAEAAEAAEAAEAAEAAEAAEAAEAAE |
| SEQ ID NO: 24 | AAEGEEEAE |
| SEQ ID NO: 25 | GGSSSGS |
| SEQ ID NO: 26 | PTPTPTP |
| SEQ ID NO: 27 | GGSSEEEAEEEAEEEAEEEAEEE |
| SEQ ID NO: 28 | GGSSSGSGGSGGSGSGGSGSGGSGSGGSGGS |
| SEQ ID NO: 29 | GGSSPTPTPTPTPTPTPTPTPTP |
| SEQ ID NO: 30 | PTPTPTPTPTPTPTPTPTPTPTPTPTP |
| SEQ ID NO: 31 | QAAAQAAAQAAAQAAAQAAAQAAAQ |
| SEQ ID NO: 32 | QAAQAAQAAQAAQAAQAAQ |
| SEQ ID NO: 33 | EAAAEAAAEAAAEAAAEAAAE |
| SEQ ID NO: 34 | DAAADAAADAAADAAADAAAD |
| SEQ ID NO: 35 | GGSSEAAAEAAAEAAAEAAAEAAAE |
| SEQ ID NO: 36 | EAAAEAAAEAAAEAAAEAAAEAAAE |
| SEQ ID NO: 37 | DAAADAAADAAADAAADAAADAAAD |
| SEQ ID NO: 38 | GGSSEAAAEAAAEAAAEAAAEAAAEAAAE |

TABLE 3

List of MIC-1 variants with corresponding SEQ ID NO.

| SEQ ID NO | MIC-1 variants |
| --- | --- |
| SEQ ID NO: 1 | Wild type human MIC-1 (hMIC-1) |
| SEQ ID NO: 14 | N3S hMIC-1 |
| SEQ ID NO: 15 | R2A, N3E hMIC-1 |
| SEQ ID NO: 16 | N3E hMIC-1 |
| SEQ ID NO: 17 | N3A hMIC-1 |
| SEQ ID NO: 18 | N3P hMIC-1 |
| SEQ ID NO: 19 | N3T hMIC-1 |
| SEQ ID NO: 20 | N3G hMIC-1 |
| SEQ ID NO: 21 | N3Q hMIC-1 |
| SEQ ID NO: 22 | N3D hMIC-1 |

TABLE 4

List of human serum albumin (HSA) variants with corresponding SEQ ID NO.

| SEQ ID NO | Human serum albumin variants |
| --- | --- |
| SEQ ID NO: 2 | Wild type HSA |
| SEQ ID NO: 23 | C34A HSA |

As a representative example, large scale production of Compound no. 7 was performed by transient expression in Expi293F cells as described in materials and methods section. Briefly, 200 µg plasmid DNA was added to 10 ml of Opti-MEM® transfection medium and 540 µl ExpiFectamine™ 293 reagent was added to 10 ml of Opti-MEM® transfection medium. The two solutions were combined to form a transfection mix. After 20 minutes incubation, the transfection mix was added to 200 ml of expi293F cell culture with a cell density of 3×106 cells/ml. 18 hours after transfection, the cultures were fed with 1 ml of enhancer 1 and 10 ml of enhancer 2. Approximately 90 hours after transfection the culture was harvested by centrifugation at 4000 g for 10 minutes. The clarified medium was sterile filtered through a 0.22 uM filter before purification.

To examine the in vivo effect of fusing a human serum albumin molecule to the N-terminus of the MIC-1 protein by variable linkers the expressed molecule were purified using the method described above. Compound no. 7 was successfully purified using automated immobilized metal ion chromatography coupled to size exclusion. Two major peaks within the total volume of the SEC column were fractioned and analysed. The first peak eluted at the void of the column and non-reducing SDS-PAGE confirmed the aggregated state of the eluted protein. The main peak partially overlapped with the aggregate peak. Therefore, not all fractions representing the entire main peak were included in the pool. Non-reducing SDS-PAGE of the pooled fractions resulted in a single band which migrated as a ~120 kDa protein. To verify the dimeric structure of the molecule, intact mass spectrometry (MS) was performed. Deconvolution of the averaged mass spectra resulted in the average mass 164140 Da. The calculated molecular weight of Compound no. 7 is 163820 Da. Thus, intact MS analysis shows that the purified molecule is in its dimeric form, but potentially carries several post translational modifications (e.g. oxidations, deamidations etc.). To further characterise the constructs, peptide mass mapping strategies were deployed for characterisation. HSA-MIC-1 fusion proteins expressed in the mammalian host cells, produced varying degree of Cys34 cysteinylation as described previously (Kleinova A, et al., Rapid Commun. Mass Spectrom, 2005; 19: 2965-2973.). In addition, it was found that other causes of heterogeniety was linked to the Asn in position 3 of the MIC-1 sequence, which was found highly labile, since it readily deamidated to Asp or isoAsp.

Pharmacological Methods

Example 2

Effect of Fusions Proteins of the Invention on Food Intake in Lean Sprague Dawley Rats The purpose of this example is to test the efficacy of the compounds in vivo. The in vivo efficacy of the compounds of the invention was measured in 250 g-300 g male non-obese Sprague Dawley rats. Animals were injected once with a dose of 4 nmol/kg body weight. Compounds were administrate subcutaneously (1 ml/kg) in a physiological isotonic phosphate buffered saline (PBS) solution (137 mM NaCL; 2.7 mM KCl; 10 mM $Na_2HPO_4$; 1.8 mM $KH_2PO_4$). In some cases the buffered saline solution also contained 500 ppm of polysorbate 80. Wild-type human MIC-1 was included as a reference compound and was injected once daily during the study with a dose of 8 nmol/kg body weight. Wild-type hMIC-1 was administered subcutaneously (1 ml/kg) in an acidic isotonic buffered solution (pH 4.0; 5 mM acetate, 2.25% glycerol, 70 ppm polysorbate 20).

Changes in food intake were measured either by an automatic food monitoring system (BioDAQ or HM-2) or by measuring the reduction in food pellets in the cage feeding tray manually over a 24 hr period of time. Animals were single housed in the BioDAQ system and housed 3 per cage in the HM-2 system. Animals were in the latter system chip-marked prior study start in order for the HM-2 system to collect individual measures of food intake. Each compound was tested in n=4-8 animals in one or more experiments. Animals were acclimatized for at least for 7 days in the experimental set up prior to study start. Collected data are expressed as daily food intake (24 hour food intake) measured from the onset of each daily 12 hour dark phase to the following dark phase. Daily changes in food intake in response to administered compound were in most studies calculated by subtracting the average daily food intake of the treatment group from the average daily food intake of the vehicle group. In a few studies daily changes in food intake in response to administered compound were calculated by subtracting the daily average food intake during the intervention from the average daily food intake of the day prior to study start. Changes were considered significant if p<0.1 using a student's t-test (two-tailed).

Several amino acid linkers between the human serum albumin part and the MIC-1 part were explored. The linkers were characterised by having different lengths, charges or structural motifs (eg. Pro-rich linkers, linkers with predicted alpha-helical propensities comprising Glu/Asp and Ala or typical Gly/Ser containing linkers conferring linker flexibility). The linker variants were evaluated and compared on basis of max efficacy, duration of biological effect and accumulated efficacy as described above.

The inventors surprisingly found that the absence of a linker or peptide linkers with a size below 10 amino acids between human serum albumin and MIC-1 resulted in compounds with limited or no significant biological efficacy (compounds 1, 2, 12, 13 and 14 (table 5)).

In contrast, linkers with a size of 10 or more amino acids positively influenced the biological efficacy of the fusion protein. In the present invention it was also found that variation in the linker amino acid composition and sequence also significantly influenced the biological efficacy of the HSA MIC-1 fusion proteins. The inventors surprisingly found that a specific combination of medium sized linkers of about 20 amino acids comprising repeats of an acidic residue (Glu or Asp) followed by at least two non-polar residues such as Ala resulted in increased biological efficacy of the HSA-MIC-1 fusion protein when compared to flexible linkers of identical size comprising Gly and Ser residues, which are normally used as linkers for separating domains of fusion proteins (Table 3, Compound no. 7 or 9 compared with Compound no. 4).

TABLE 5

Effect of a single dose (4 nmol/kg) of comparative HSA-MIC-1 fusion proteins on daily food intake in lean SD rats. Data are expressed in 3 ways, 1) maximum efficacy which is the greatest significant (p < 0.10) reduction in 24 hours food intake recorded over the study period, 2) Accumulated efficacy which is the sum of significant (p < 0.10) reductions in 24 hours food intake compared with vehicle and 3) Duration of effect which is the number of days with a significant (p < 0.1) reductions in food intake compared with vehicle. Wild-type human MIC-1 is included for comparison and was administered once daily for 7 days (8 nmol/kg).

| Compound | Length of linker (number of amino acids) | Maximum efficacy | Accumulated efficacy | Duration of effect |
| --- | --- | --- | --- | --- |
| wt MIC-1 (SEQ ID NO: 1) | 0 | 37 | n/a | 1 |
| 1 | 0 | 0 | 0 | 0 |
| 2 | 7 | 11 | 11 | 1 |
| 12 | 9 | 11 | 8 | 1 |
| 13 | 7 | −12 | −12 | 1 |
| 14 | 7 | 15 | 1 | 2 |
| 8 | 19 | 23 | 66 | 3 |
| 3 | 19 | 30 | 74 | 4 |
| 15 | 23 | 20 | 38 | 2 |
| 4 | 23 | 28 | 72 | 3 |
| 16 | 31 | 22 | 56 | 3 |
| 6 | 19 | 18 | 34 | 2 |
| 17 | 23 | 30 | 78 | 3 |
| 18 | 31 | 23 | 23 | 1 |
| 19 | 25 | 20 | 51 | 3 |
| 20 | 19 | 30 | 83 | 3 |

TABLE 6

Effect of a single dose (4 nmol/kg) of HSA-MIC-1 fusion proteins of the invention having varying linker length on daily food intake in lean SD rats. Data are expressed in 3 ways, 1) maximum efficacy which is the greatest significant(p < 0.10) reduction in 24 hours food intake recorded over the study period, 2) Accumulated efficacy which is the sum of significant (p < 0.10) reductions in 24 hours food intake compared with vehicle and 3) Duration of effect which is the number of days with a significant (p < 0.1) reductions in food intake compared with vehicle. Wild-type human MIC-1 is included for comparison and was administered once daily for 7 days (8 nmol/kg).

| Compound | Length of linker (number of amino acids) | Maximum efficacy | Accumulated efficacy | Duration of effect |
| --- | --- | --- | --- | --- |
| wt MIC-1 (SEQ ID NO: 1) | 0 | 37 | n/a | 1 |
| 5 | 19 | 42 | 183 | 6 |
| g | 19 | 35 | 86 | 4 |
| 21 | 21 | 33 | 80 | 3 |
| 22 | 21 | 39 | 183 | 6 |
| 7 | 23 | 39 | 167 | 6 |
| 23 | 23 | 31 | 98 | 4 |
| 33 | 25 | 37 | 154 | 5 |
| 34 | 25 | 31 | 135 | 5 |
| 35 | 25 | 38 | 149 | 5 |
| 36 | 29 | 39 | 169 | 6 |
| 10 | 31 | 31 | 91 | 4 |
| 11 | 35 | 25 | 60 | 3 |

More in particular, the inventors surprisingly found that medium sized linkers of about 10-35 amino acids comprising repeats of an acidic residue (Glu or Asp) followed by at least two non-polar residues such as Ala showed favorable biological efficacy of the HSA-MIC-1 fusion protein, when compared to flexible linkers of identical size comprising Gly and Ser residues or rigid Pro containing linkers (compound 7 (table 6) compared with compounds 4 and 17 (table 5)). Similar observations were done for longer linkers above 30 aa (compound 10 (table 6) compared with compound 16 or 18 (table 5)). Substitutions of Ala with acidic residues in each repeat negatively affected the maximum efficacy and/or accumulated efficacy (e.g. compound 5 (table 6) compared to compound 8 (table 5)). Surprisingly, it was found that substitution of the acidic residues of linkers containing repeats of Glu-Ala-Ala or Asp-Ala-Ala with a basic Lys residue resulted in a clear decrease in biological efficacy and accumulated food intake demonstrating that difference in efficacy can result from small changes in the linker sequence (Compound no. 5 and 9 (table 6) compared to compound 6 (table 5)).

Thus, the present invention demonstrates that HSA MIC-1 fusion proteins with certain linkers results in higher maximum efficacy and accumulated efficacy as well as longer duration of the fusion protein.

TABLE 7

Effect of a single dose (4 nmol/kg) of HSA-MIC-1 fusion proteins of the invention all having a linker of SEQ ID NO: 9, and comprising a MIC-1 variant and/or human serum albumin variant on daily food intake in lean SD rats. Data are expressed in 3 ways, 1) maximum efficacy which is the greatest significant (p < 0.10) reduction in 24 hours food intake recorded over the study period, 2) Accumulated efficacy which is the sum of significant (p < 0.10) reductions in 24 hours food intake compared with vehicle and 3) Duration of effect which is the number of days with a significant (p < 0.1) reductions in food intake compared with vehicle. Wild-type hMIC-1 is included for comparison and was administered once daily for 7 days (8 nmol/kg).

| Compound | HSA variant | MIC-1/ MIC-1 variant | Maximum efficacy | Accumulated efficacy | Duration of effect |
| --- | --- | --- | --- | --- | --- |
| wt MIC-1 (SEQ ID NO: 1) | — | — | 37 | n/a | 1 |
| 24 | SEQ ID NO: 23 | SEQ ID NO: 1 | 29 | 69 | 3 |
| 25 | SEQ ID NO: 23 | SEQ ID NO: 14 | 38 | 127 | 5 |
| 26 | SEQ ID NO: 23 | SEQ ID NO: 15 | 30 | 114 | 5 |
| 27 | SEQ ID NO: 23 | SEQ ID NO: 16 | 31 | 87 | 3 |
| 28 | SEQ ID NO: 23 | SEQ ID NO: 17 | 31 | 89 | 4 |
| 29 | SEQ ID NO: 23 | SEQ ID NO: 18 | 38 | 78 | 3 |
| 30 | SEQ ID NO: 23 | SEQ ID NO: 19 | 22 | 54 | 3 |
| 31 | SEQ ID NO: 23 | SEQ ID NO: 20 | 30 | 74 | 3 |
| 32 | SEQ ID NO: 23 | SEQ ID NO: 21 | 34 | 113 | 4 |
| 37 | SEQ ID NO: 23 | SEQ ID NO: 22 | 44 | 173 | 5 |

HSA MIC-1 fusions proteins, all with a linker of SEQ ID NO:9, and comprising the MIC-1 variants and/or the human serum albumin variants of tables 3 and 4, respectively, were prepared and tested to investigate if these changes in the MIC-1 part and/or the human serum albumin part had an effect on the efficacy of the fusion proteins. As can be seen in table 7, all the fusions proteins were found to significantly reduce food intake for 3-5 days in response to a single injection of 4 nmol/kg.

Example 3

Effect of Fusions Proteins of the Invention on Food Intake in DIO Sprague Dawley Rats DIO rats were used to further study compounds tested in lean rats. Obesity was induced by placing eight-week-old animals on a special research diet (Research Diets, D12451) where 45% of the energy content is derived from fat. Animals typically reached a body weight of 500-600 g before study initiation. Animals were injected once with a dose of 4 nmol/kg body weight. Compounds were administered subcutaneously (1 ml/kg) in a physiological isotonic phosphate buffered saline (PBS) solution (137 mM NaCL; 2.7 mM KCl; 10 mM $Na_2HPO_4$; 1.8 mM $KH_2PO_4$). In some cases the buffered saline solution also contained 500 ppm of polysorbate 80.

Changes in food intake were measured by an automatic food monitoring system (BioDAQ or HM-2). Animals were single housed in the BioDAQ system and housed 3 per cage in the in the HM-2 system. Animals were in the latter system chip-marked prior to study start in order for the HM-2 system to collect individual measures of food intake. Each compound was tested in n=4-8 animals in one or more experiments. Animals were acclimatized for at least 7 days in the experimental set up prior to study start. Collected food intake data are expressed as daily food intake (24 hour food intake) measure from the onset of each daily 12 hour dark phase to the following dark phase. Daily changes in food intake in response to administered compound were calculated by subtracting the average daily food intake of the treatment group from the average daily food intake of the vehicle group. Changes were considered significant if p<0.1 using a student's t-test (two-tailed).

The HSA MIC-1 fusion proteins tested all displayed good efficacy in DIO rats. When comparing compound 7 and 23, it is apparent that the His-tag (SEQ ID NO:3) does not affect the efficacy or duration of effect of the fusion proteins.

TABLE 8

Effect of a single dose (4 nmol/kg) of HSA-MIC-1 analogues on body weight and daily food intake in obese SD rats. Data are expressed in 4 ways, 1) maximum efficacy which is the greatest significant (p < 0.10) reduction in 24 hours food intake recorded over the study period, 2) Accumulated efficacy which is the sum of significant (p < 0.10) reductions in 24 hours food intake compared with vehicle and 3) Duration of effect which is the number of days with a significant (p < 0.1) reductions in food intake compared with vehicle, 4) Differences in body weight at day 7 compared to the vehicle group.

| Compound | Maximum efficacy | Accumulated efficacy | Duration of effect | % body weight difference |
|---|---|---|---|---|
| 5 | 61 | 309 | 6 | −6.7 |
| 7 | 68 | 369 | 6 | −8.9 |
| 9 | 56 | 331 | 7 | −7.1 |
| 23 | 70 | 355 | 7 | −8.8 |
| 24 | 62 | 331 | 6 | −10 |
| 26 | 64 | 385 | 7 | −9.6 |

Example 4

Pharmacokinetic Evaluation of MIC-1 Compounds in Lean Sprague Dawley Rats

The purpose of this study is to determine the half-life in vivo of the HSA MIC-1 fusion proteins after intravenous administration to lean Sprague Dawley rats, i.e. the prolongation of their time in the blood circulation and thereby their time of action. This is done in a pharmacokinetic (PK) study, where the terminal half-life of the fusion protein in question is determined. By terminal half-life is generally meant the period of time it takes to halve a certain plasma concentration, measured after the initial distribution phase.

The in vivo half-life was measured in 300 g-500 g lean SD rats by injecting the compound into the tail vein followed by collection of blood plasma samples at various time points for exposure analysis. Compounds (0.5 nmol/kg body weight) were administered intravenously (1 ml/kg) in a physiologically isotonic phosphate buffered saline (PBS) solution (140 mM NaCL; 2.7 mM KCl; 8.05 mM $Na_2HPO_4$; 1.96 mM $KH_2PO_4$, 500 ppm polysorbate 80). Blood samples were collected from the tongue at time −30, 30, 60, 240 and 420 minutes and 24, 30, 48, 72, 96, 120, 168, 216, 264 and 360/384 hours. 200 µl of blood was collected into EDTA tubes and stored on ice for up to 20 minutes. Plasma samples were generated by centrifuging blood samples for 5 minutes at 10000 G at 4° C. The sample was subsequent pipetted into Micronic tubes on dry ice, and kept at −20° C. until analysed for plasma concentration of the respective MIC-1 compound using LOCI or a similar antibody based assay such as ELISA. The individual plasma concentration-time profiles were analysed by a non-compartmental model in Phoenix v. 6.2 or 6.3 software (Pharsight Inc., Mountain View, Calif., USA), and the resulting terminal half-lives determined.

TABLE 9

Pharmacokinetic profile of MIC-1 compounds in lean SD rats (0.5 nmol/kg) with intravenous tail vein dosing. Data are expressed as the half-life (T½).

| Compound | intravenous T½ (hours) |
|---|---|
| wt hMIC-1 (SEQ ID NO: 1) | 1.9 |
| 1 | 38 |
| 2 | 32 |

TABLE 9-continued

Pharmacokinetic profile of MIC-1 compounds in lean SD rats (0.5 nmol/kg) with intravenous tail vein dosing. Data are expressed as the half-life (T½).

| Compound | intravenous T½ (hours) |
|---|---|
| 3 | 27 |
| 4 | 29 |
| 5 | 27 |
| 6 | 27 |
| 7 | 36 |
| 8 | 19 |
| 9 | 37 |
| 10 | 22 |
| 13 | 27 |
| 14 | 41 |
| 16 | 30 |
| 18 | 45 |
| 20 | 35 |
| 21 | 39 |
| 23 | 46 |
| 24 | 42 |
| 25 | 38 |
| 26 | 49 |
| 33 | 36 |
| 35 | 31 |
| 36 | 37 |

A correlation between the length of the linker (i.e—the number of amino acids in the linker) and the T½ in lean rat was analysed using a Pearson correlation analysis. The Spearman correlation coefficient was −0.0365 suggesting no significant linear relationship between the linker length and T½. An implication of this analysis is that the biological efficacy of the fusion proteins is not a function of the in vivo half-life of the fusion proteins.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A fusion protein of formula (I):

$$A\text{-}B\text{—}C \qquad (I),$$

wherein
A is human serum albumin or a functional variant thereof;
B is a peptide linker having the amino acid sequence of SEQ ID NO:9; and
C is a MIC-1 protein or an analogue thereof,
wherein the C-terminus of the human serum albumin or functional variant thereof is fused to the N-terminus of the peptide linker, and
wherein the C-terminus of the peptide linker is fused to the N-terminus of the MIC-1 protein or analogue thereof.

2. The fusion protein according to claim 1, wherein C is a MIC-1 analogue having at least 95% sequence identity to SEQ ID NO:1.

3. The fusion protein according to claim 1, wherein C is selected from the group consisting of a native MIC-1 protein having the amino acid sequence of SEQ ID NO:1, a MIC-1 analogue having the amino acid sequence of SEQ ID NO:14, and a MIC-1 analogue having the amino acid sequence of SEQ ID NO:15.

4. The fusion protein according to claim 1, wherein A is a human serum albumin functional variant having at least 95% sequence identity to SEQ ID NO:2.

5. The fusion protein according to claim 1, wherein A is selected from the group consisting of wild type human serum albumin having the amino acid sequence of SEQ ID NO:2 and a human serum albumin functional variant having the amino acid sequence of SEQ ID NO:23.

6. The fusion protein according to claim 1, wherein A is human serum albumin protein with the amino acid sequence of SEQ ID NO:2 and C is a native human MIC-1 having the amino acid sequence of SEQ ID NO:1.

7. The fusion protein according to claim 1, wherein A is a human serum albumin protein variant having the amino acid sequence of SEQ ID NO:23 and C is a native human MIC-1 having the amino acid sequence of SEQ ID NO:1.

8. The fusion protein according to claim 1, wherein A is a human serum albumin protein variant having the amino acid sequence of SEQ ID NO:23 and C is a MIC-1 analogue having the amino acid sequence of SEQ ID NO:14.

9. The fusion protein according to claim 1, wherein A is a human serum albumin protein variant having the amino acid sequence of SEQ ID NO:23 and C is a MIC-1 analogue having the amino acid sequence of SEQ ID NO:15.

10. A compound comprising a homodimer of a fusion protein of formula (I):

A-B—C     (I), wherein

A is human serum albumin or a functional variant thereof;
B is a peptide linker having the amino acid sequence of SEQ ID NO:9; and
C is a MIC-1 protein or an analogue thereof,
wherein the C-terminus of the human serum albumin or functional variant thereof is fused to the N-terminus of the peptide linker,
wherein the C-terminus of the peptide linker is fused to the N-terminus of the MIC-1 protein or analogue thereof, and
wherein the homodimer comprises an interchain disulphide bridge between the MIC-1 protein or analogue thereof of each fusion protein.

11. A pharmaceutical composition comprising a fusion protein of formula (I):

A-B—C     (I), wherein

A is human serum albumin or a functional variant thereof;
B is a peptide linker having the amino acid sequence of SEQ ID NO:9; and
C is a MIC-1 protein or an analogue thereof,
wherein the C-terminus of the human serum albumin or functional variant thereof is fused to the N-terminus of the peptide linker, and
wherein the C-terminus of the peptide linker is fused to the N-terminus of the MIC-1 protein or analogue thereof;
or a pharmaceutically acceptable salt, amide, or ester thereof.

12. The pharmaceutical composition according to claim 11, wherein
A is human serum albumin protein with the amino acid sequence of SEQ ID NO:2 and C is a native human MIC-1 having the amino acid sequence of SEQ ID NO:1.

13. The pharmaceutical composition according to claim 12, further comprising a homodimer of the fusion protein, wherein the homodimer comprises an interchain disulphide bridge between the native human MIC-1 of each fusion protein.

14. The pharmaceutical composition according to claim 11, wherein A is a human serum albumin protein variant having the amino acid sequence of SEQ ID NO:23 and C is a native human MIC-1 having the amino acid sequence of SEQ ID NO:1.

15. The pharmaceutical composition according to claim 14, further comprising a homodimer of the fusion protein, wherein the homodimer comprises an interchain disulphide bridge between the native human MIC-1 of each fusion protein.

16. The pharmaceutical composition according to claim 11, wherein A is a human serum albumin protein variant having the amino acid sequence of SEQ ID NO:23 and C is a MIC-1 analogue having the amino acid sequence of SEQ ID NO:14.

17. The pharmaceutical composition according to claim 16, further comprising a homodimer of the fusion protein, wherein the homodimer comprises an interchain disulphide bridge between the MIC-1 analogue of each fusion protein.

18. The pharmaceutical composition according to claim 11, wherein A is a human serum albumin protein variant having the amino acid sequence of SEQ ID NO:23 and C is a MIC-1 analogue having the amino acid sequence of SEQ ID NO:15.

19. The pharmaceutical composition according to claim 18, further comprising a homodimer of the fusion protein, wherein the homodimer comprises an interchain disulphide bridge between the MIC-1 analogue of each fusion protein.

20. A method of treating an eating disorder by administering a pharmaceutically active amount of a fusion protein of formula (I):

A-B—C     (I), wherein

A is human serum albumin or a functional variant thereof;
B is a peptide linker having the amino acid sequence of SEQ ID NO:9; and
C is a MIC-1 protein or an analogue thereof,
wherein the C-terminus of the human serum albumin or functional variant thereof is fused to the N-terminus of the peptide linker, and
wherein the C-terminus of the peptide linker is fused to the N-terminus of the MIC-1 protein or analogue thereof.

21. The method according to claim 20, wherein the eating disorder is obesity.

22. The method according to claim 21, wherein A is human serum albumin protein with the amino acid sequence of SEQ ID NO:2 and C is a native human MIC-1 having the amino acid sequence of SEQ ID NO:1.

23. The method according to claim 22, further comprising a homodimer of the fusion protein, wherein the homodimer comprises an interchain disulphide bridge between the native human MIC-1 of each fusion protein.

24. The method according to claim 21, wherein A is a human serum albumin protein variant having the amino acid sequence of SEQ ID NO:23 and C is a native human MIC-1 having the amino acid sequence of SEQ ID NO:1.

25. The method according to claim 24, further comprising a homodimer of the fusion protein, wherein the homodimer comprises an interchain disulphide bridge between the native human MIC-1 of each fusion protein.

26. The method according to claim 21, wherein A is a human serum albumin protein variant having the amino acid sequence of SEQ ID NO:23 and C is a MIC-1 analogue having the amino acid sequence of SEQ ID NO:14.

27. The method according to claim 26, further comprising a homodimer of the fusion protein, wherein the homodimer comprises an interchain disulphide bridge between the MIC-1 analogue of each fusion protein.

28. The method according to claim 21, wherein A is a human serum albumin protein variant having the amino acid sequence of SEQ ID NO:23 and C is a MIC-1 analogue having the amino acid sequence of SEQ ID NO:15.

29. The method according to claim 28, further comprising a homodimer of the fusion protein, wherein the homodimer comprises an interchain disulphide bridge between the MIC-1 analogue of each fusion protein.

* * * * *

SEQUENCE LISTING

<160> NUMBER OF SEQ ID NOS: 40

<210> SEQ ID NO 1
<211> LENGTH: 112
<212> TYPE: PRT
<213> ORGANISM: HOMO SAPIENS

<400> SEQUENCE: 1

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 2
<211> LENGTH: 585
<212> TYPE: PRT
<213> ORGANISM: HOMO SAPIENS

<400> SEQUENCE: 2

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
```

```
                50                  55                  60
    Ser Leu His Thr Leu Phe Gly Asp Lys Leu Cys Thr Val Ala Thr Leu
    65                      70                  75                  80

Arg Glu Thr Tyr Gly Glu Met Ala Asp Cys Cys Ala Lys Gln Glu Pro
                        85                  90                  95

Glu Arg Asn Glu Cys Phe Leu Gln His Lys Asp Asp Asn Pro Asn Leu
                    100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
    145                 150                 155                 160

Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
    225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
                290                 295                 300

Leu Ala Ala Asp Phe Val Glu Ser Lys Asp Val Cys Lys Asn Tyr Ala
    305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
    385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
    465                 470                 475                 480
```

```
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 3
<211> LENGTH: 11
<212> TYPE: PRT
<213> ORGANISM: ARTIFICIAL
<220> FEATURE:
<223> OTHER INFORMATION: His-tag

<400> SEQUENCE: 3

His His His His His His Gly Gly Gly Ser Ser
1               5                   10

<210> SEQ ID NO 4
<211> LENGTH: 7
<212> TYPE: PRT
<213> ORGANISM: ARTIFICIAL
<220> FEATURE:
<223> OTHER INFORMATION: peptide linker

<400> SEQUENCE: 4

Glu Ala Ala Glu Ala Ala Glu
1               5

<210> SEQ ID NO 5
<211> LENGTH: 19
<212> TYPE: PRT
<213> ORGANISM: ARTIFICIAL
<220> FEATURE:
<223> OTHER INFORMATION: peptide linker

<400> SEQUENCE: 5

Glu Glu Glu Ala Glu Glu Glu Ala Glu Glu Glu Ala Glu Glu Glu Ala
1               5                   10                  15

Glu Glu Glu

<210> SEQ ID NO 6
<211> LENGTH: 23
<212> TYPE: PRT
<213> ORGANISM: ARTIFICIAL
<220> FEATURE:
<223> OTHER INFORMATION: peptide linker

<400> SEQUENCE: 6

Gly Gly Ser Ser Ser Gly Ser Gly Ser Gly Gly Ser Gly Ser Gly Gly
1               5                   10                  15

Gly Ser Gly Gly Ser Gly Ser
            20
```

```
<210> SEQ ID NO 7
<211> LENGTH: 19
<212> TYPE: PRT
<213> ORGANISM: ARTIFICIAL
<220> FEATURE:
<223> OTHER INFORMATION: peptide linker

<400> SEQUENCE: 7

Asp Asp Ala Asp Asp Ala Asp Asp Ala Asp Asp Ala Asp Asp Ala Asp
1               5                   10                  15

Asp Ala Asp

<210> SEQ ID NO 8
<211> LENGTH: 19
<212> TYPE: PRT
<213> ORGANISM: ARTIFICIAL
<220> FEATURE:
<223> OTHER INFORMATION: peptide linker

<400> SEQUENCE: 8

Lys Ala Ala Lys Ala Ala Lys Ala Ala Lys Ala Ala Lys Ala Ala Lys
1               5                   10                  15

Ala Ala Lys

<210> SEQ ID NO 9
<211> LENGTH: 23
<212> TYPE: PRT
<213> ORGANISM: ARTIFICIAL
<220> FEATURE:
<223> OTHER INFORMATION: peptide linker

<400> SEQUENCE: 9

Gly Gly Ser Ser Glu Ala Ala Glu Ala Ala Glu Ala Ala Glu Ala Ala
1               5                   10                  15

Glu Ala Ala Glu Ala Ala Glu
            20

<210> SEQ ID NO 10
<211> LENGTH: 19
<212> TYPE: PRT
<213> ORGANISM: ARTIFICIAL
<220> FEATURE:
<223> OTHER INFORMATION: peptide linker

<400> SEQUENCE: 10

Asp Ala Ala Asp Ala Ala Asp Ala Ala Asp Ala Ala Asp Ala Ala Asp
1               5                   10                  15

Ala Ala Asp

<210> SEQ ID NO 11
<211> LENGTH: 19
<212> TYPE: PRT
<213> ORGANISM: ARTIFICIAL
<220> FEATURE:
<223> OTHER INFORMATION: peptide linker

<400> SEQUENCE: 11

Glu Ala Ala Glu Ala Ala Glu Ala Ala Glu Ala Ala Glu Ala Ala Glu
1               5                   10                  15

Ala Ala Glu

<210> SEQ ID NO 12
<211> LENGTH: 31
```

```
<212> TYPE: PRT
<213> ORGANISM: ARTIFICIAL
<220> FEATURE:
<223> OTHER INFORMATION: peptide linker

<400> SEQUENCE: 12

Glu Ala Ala Glu Ala Ala Glu Ala Ala Glu Ala Glu Ala Ala Glu
1               5                   10                  15

Ala Ala Glu Ala Ala Glu Ala Ala Glu Ala Ala Glu Ala Ala Glu
            20                  25                  30

<210> SEQ ID NO 13
<211> LENGTH: 35
<212> TYPE: PRT
<213> ORGANISM: ARTIFICIAL
<220> FEATURE:
<223> OTHER INFORMATION: peptide linker

<400> SEQUENCE: 13

Gly Gly Ser Ser Glu Ala Ala Glu Ala Ala Glu Ala Ala Glu Ala Ala
1               5                   10                  15

Glu Ala Ala Glu Ala Ala Glu Ala Ala Glu Ala Ala Glu Ala Ala Glu
            20                  25                  30

Ala Ala Glu
        35

<210> SEQ ID NO 14
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 14

Ala Arg Ser Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 15
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 15

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30
```

```
Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 16
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 16

```
Ala Arg Glu Gly Asp His Cys Pro Leu Gly Pro Gly Arg Cys Cys Arg
1                5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 17
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 17

```
Ala Arg Ala Gly Asp His Cys Pro Leu Gly Pro Gly Arg Cys Cys Arg
1                5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 18

```
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 18

Ala Arg Pro Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 19
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 19

Ala Arg Thr Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 20
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 20

Ala Arg Gly Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45
```

```
Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 21
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 21

```
Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 22
<211> LENGTH: 112
<212> TYPE: PRT
<213> ORGANISM: ARTIFICIAL
<220> FEATURE:
<223> OTHER INFORMATION: MIC-1 analogue

<400> SEQUENCE: 22

```
Ala Arg Asp Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 23
<211> LENGTH: 585
<212> TYPE: PRT
<213> ORGANISM: ARTIFICIAL

<220> FEATURE:
<223> OTHER INFORMATION: variant of human serum albumin

<400> SEQUENCE: 23

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 24
<211> LENGTH: 9
<212> TYPE: PRT
<213> ORGANISM: ARTIFICIAL
<220> FEATURE:
<223> OTHER INFORMATION: peptide linker

<400> SEQUENCE: 24

Ala Ala Glu Gly Glu Glu Glu Ala Glu
1               5

<210> SEQ ID NO 25
<211> LENGTH: 7
<212> TYPE: PRT
<213> ORGANISM: ARTIFICIAL
<220> FEATURE:
<223> OTHER INFORMATION: peptide linker

<400> SEQUENCE: 25

Gly Gly Ser Ser Ser Gly Ser
1               5

<210> SEQ ID NO 26
<211> LENGTH: 7
<212> TYPE: PRT
<213> ORGANISM: ARTIFICIAL
<220> FEATURE:
<223> OTHER INFORMATION: peptide linker

<400> SEQUENCE: 26

Pro Thr Pro Thr Pro Thr Pro
1               5

<210> SEQ ID NO 27
<211> LENGTH: 23
```

```
<212> TYPE: PRT
<213> ORGANISM: ARTIFICIAL
<220> FEATURE:
<223> OTHER INFORMATION: peptide linker

<400> SEQUENCE: 27

Gly Gly Ser Ser Glu Glu Ala Glu Glu Ala Glu Glu Ala
1               5                   10                  15

Glu Glu Glu Ala Glu Glu Glu
            20

<210> SEQ ID NO 28
<211> LENGTH: 31
<212> TYPE: PRT
<213> ORGANISM: ARTIFICIAL
<220> FEATURE:
<223> OTHER INFORMATION: peptide linker

<400> SEQUENCE: 28

Gly Gly Ser Ser Ser Gly Ser Gly Gly Ser Gly Gly Ser Gly
1               5                   10                  15

Gly Ser Gly Gly Ser Gly Ser Gly Gly Ser Gly Gly Ser
            20                  25                  30

<210> SEQ ID NO 29
<211> LENGTH: 23
<212> TYPE: PRT
<213> ORGANISM: ARTIFICIAL
<220> FEATURE:
<223> OTHER INFORMATION: peptide linker

<400> SEQUENCE: 29

Gly Gly Ser Ser Pro Thr Pro Thr Pro Thr Pro Thr Pro Thr
1               5                   10                  15

Pro Thr Pro Thr Pro Thr Pro
            20

<210> SEQ ID NO 30
<211> LENGTH: 31
<212> TYPE: PRT
<213> ORGANISM: ARTIFICIAL
<220> FEATURE:
<223> OTHER INFORMATION: peptide linker

<400> SEQUENCE: 30

Pro Thr Pro Thr Pro Thr Pro Thr Pro Thr Pro Thr Pro Thr
1               5                   10                  15

Pro Thr Pro Thr Pro Thr Pro Thr Pro Thr Pro Thr Pro
            20                  25                  30

<210> SEQ ID NO 31
<211> LENGTH: 25
<212> TYPE: PRT
<213> ORGANISM: ARTIFICIAL
<220> FEATURE:
<223> OTHER INFORMATION: peptide linker

<400> SEQUENCE: 31

Gln Ala Ala Ala Gln Ala Ala Ala Gln Ala Ala Ala Gln Ala Ala
1               5                   10                  15

Gln Ala Ala Ala Gln Ala Ala Ala Gln
            20                  25

<210> SEQ ID NO 32
```

```
<211> LENGTH: 19
<212> TYPE: PRT
<213> ORGANISM: ARTIFICIAL
<220> FEATURE:
<223> OTHER INFORMATION: peptide linker

<400> SEQUENCE: 32

Gln Ala Ala Gln Ala Ala Gln Ala Ala Gln Ala Ala Gln Ala Ala Gln
1               5                   10                  15

Ala Ala Gln

<210> SEQ ID NO 33
<211> LENGTH: 21
<212> TYPE: PRT
<213> ORGANISM: ARTIFICIAL
<220> FEATURE:
<223> OTHER INFORMATION: peptide linker

<400> SEQUENCE: 33

Glu Ala Ala Ala Glu Ala Ala Ala Glu Ala Ala Ala Glu Ala Ala Ala
1               5                   10                  15

Glu Ala Ala Ala Glu
                20

<210> SEQ ID NO 34
<211> LENGTH: 21
<212> TYPE: PRT
<213> ORGANISM: ARTIFICIAL
<220> FEATURE:
<223> OTHER INFORMATION: peptide linker

<400> SEQUENCE: 34

Asp Ala Ala Ala Asp Ala Ala Ala Asp Ala Ala Ala Asp Ala Ala Ala
1               5                   10                  15

Asp Ala Ala Ala Asp
                20

<210> SEQ ID NO 35
<211> LENGTH: 25
<212> TYPE: PRT
<213> ORGANISM: ARTIFICIAL
<220> FEATURE:
<223> OTHER INFORMATION: peptide linker

<400> SEQUENCE: 35

Gly Gly Ser Ser Glu Ala Ala Ala Glu Ala Ala Ala Glu Ala Ala Ala
1               5                   10                  15

Glu Ala Ala Ala Glu Ala Ala Ala Glu
                20                  25

<210> SEQ ID NO 36
<211> LENGTH: 25
<212> TYPE: PRT
<213> ORGANISM: ARTIFICIAL
<220> FEATURE:
<223> OTHER INFORMATION: peptide linker

<400> SEQUENCE: 36

Glu Ala Ala Ala Glu Ala Ala Ala Glu Ala Ala Ala Glu Ala Ala Ala
1               5                   10                  15

Glu Ala Ala Ala Glu Ala Ala Ala Glu
                20                  25

<210> SEQ ID NO 37
```

```
<211> LENGTH: 25
<212> TYPE: PRT
<213> ORGANISM: ARTIFICIAL
<220> FEATURE:
<223> OTHER INFORMATION: peptide linker

<400> SEQUENCE: 37

Asp Ala Ala Ala Asp Ala Ala Ala Asp Ala Ala Ala Asp Ala Ala
1               5                   10                  15

Asp Ala Ala Ala Asp Ala Ala Ala Asp
            20                  25

<210> SEQ ID NO 38
<211> LENGTH: 29
<212> TYPE: PRT
<213> ORGANISM: ARTIFICIAL
<220> FEATURE:
<223> OTHER INFORMATION: peptide linker

<400> SEQUENCE: 38

Gly Gly Ser Ser Glu Ala Ala Ala Glu Ala Ala Ala Glu Ala Ala
1               5                   10                  15

Glu Ala Ala Ala Glu Ala Ala Ala Glu Ala Ala Ala Glu
            20                  25

<210> SEQ ID NO 39
<211> LENGTH: 18
<212> TYPE: PRT
<213> ORGANISM: Artificial Sequence
<220> FEATURE:
<223> OTHER INFORMATION: peptide linker

<400> SEQUENCE: 39

Glu Ala Ala Glu Ala Ala Glu Ala Ala Glu Ala Ala Glu Ala Ala Glu
1               5                   10                  15

Ala Ala

<210> SEQ ID NO 40
<211> LENGTH: 4
<212> TYPE: PRT
<213> ORGANISM: Artificial Sequence
<220> FEATURE:
<223> OTHER INFORMATION: Synthetic

<400> SEQUENCE: 40

Gly Gly Ser Ser
1
```